United States Patent
Nguyen

(10) Patent No.: US 10,664,489 B1
(45) Date of Patent: May 26, 2020

(54) APPARATUS, METHOD, AND SYSTEM OF COGNITIVE DATA BLOCKS AND LINKS FOR PERSONALIZATION, COMPREHENSION, RETENTION, AND RECALL OF COGNITIVE CONTENTS OF A USER

(71) Applicant: FUVI COGNITIVE NETWORK CORP., Framingham, MA (US)

(72) Inventor: Phu-Vinh Nguyen, Sherborn, MA (US)

(73) Assignee: FUVI COGNITIVE NETWORK CORP., Framingham, MA (US)

( * ) Notice: Subject to any disclaimer, the term of this patent is extended or adjusted under 35 U.S.C. 154(b) by 0 days.

(21) Appl. No.: 16/535,699

(22) Filed: Aug. 8, 2019

Related U.S. Application Data

(60) Provisional application No. 62/768,258, filed on Nov. 16, 2018.

(51) Int. Cl.
*G06F 16/248* (2019.01)
*G06F 9/451* (2018.01)
*G06F 16/27* (2019.01)

(52) U.S. Cl.
CPC .......... *G06F 16/248* (2019.01); *G06F 9/451* (2018.02); *G06F 16/27* (2019.01)

(58) Field of Classification Search
CPC . A61B 5/7275; A61B 5/1114; A61B 5/14552; A61B 5/04; G06F 19/3418; G06F 19/00; G06F 3/012
USPC .......... 707/600–831, 899, 999.001–999.206
See application file for complete search history.

(56) References Cited

U.S. PATENT DOCUMENTS

| | | | |
|---|---|---|---|
| 9,711,056 B1 | 7/2017 | Nguyen | |
| 9,886,493 B2 * | 2/2018 | Coleman | .......... G06F 16/24578 |
| 10,127,825 B1 | 11/2018 | Nguyen | |
| 10,367,931 B1 | 7/2019 | Nguyen | |
| 10,373,510 B2 | 8/2019 | Nguyen | |
| 2013/0011819 A1 * | 1/2013 | Horseman | ............ A61B 5/6887 |
| | | | 434/257 |
| 2014/0310595 A1 * | 10/2014 | Acharya | ................. G06F 9/453 |
| | | | 715/706 |
| 2014/0323142 A1 * | 10/2014 | Rodriguez | .......... G06F 3/04842 |
| | | | 455/452.1 |
| 2015/0163345 A1 * | 6/2015 | Cornaby | ............... G06F 1/1686 |
| | | | 345/633 |
| 2015/0248470 A1 * | 9/2015 | Coleman | .......... G06F 16/24578 |
| | | | 707/740 |
| 2015/0290453 A1 | 10/2015 | Tyler et al. | |

(Continued)

OTHER PUBLICATIONS

Ha et al., "Towards Wearable Cognitive Assistance", Dec. 31, 2013, 26 pages. retrieved from Internet Jan. 21, 2020; https://apps.dtic.mil/dtic/tr/fulltext/u2/a591470.pdf.

(Continued)

*Primary Examiner* — Angelica Ruiz
(74) *Attorney, Agent, or Firm* — Edell, Shapiro & Finnan, LLC

(57) ABSTRACT

A cognitive assistant system which includes one or more components which may be worn or carried by a user for capturing sensory data of the user. The cognitive assistant system further includes a processor which processes captured data for structuring cognitive cued database and for an episodic cue-based display and navigation, which facilitates comprehension and effective recall of information to a particular user.

20 Claims, 22 Drawing Sheets

(56) References Cited

U.S. PATENT DOCUMENTS

| | | | |
|---|---|---|---|
| 2017/0160813 A1 | 8/2017 | Divakaran et al. | |
| 2017/0221072 A1* | 8/2017 | AthuluruTlrumala | ........................ G06Q 30/016 |
| 2017/0328726 A1* | 11/2017 | Matsuzawa | ............ G01C 21/26 |
| 2017/0337476 A1* | 11/2017 | Gordon | .................. G06N 5/022 |
| 2017/0351330 A1* | 12/2017 | Gordon | .................. G06F 1/163 |

OTHER PUBLICATIONS

International Search Report and Written Opinion in counterpart International Application No. PCT/US2019/059038, dated Jan. 13, 2020, 8 pages.

* cited by examiner

APPARATUS, METHOD, AND SYSTEM OF COGNITIVE DATA BLOCKS AND LINKS FOR PERSONALIZATION, COMPREHENSION, RETENTION, AND RECALL OF COGNITIVE CONTENTS OF A USER

CROSS-REFERENCE TO RELATED APPLICATION

This application claims priority from U.S. Provisional Application No. 62/768,258, filed on Nov. 16, 2018, the contents of which are incorporated herein by reference in its entirety.

BACKGROUND

1. Field

Apparatuses, methods, systems, and computer readable mediums consistent with exemplary embodiments broadly relate to cognitive technology.

2. Description of Related Art

Nowadays, the world of information grows exponentially. People are challenged to receive and retain vast amounts of information in their daily lives. In order to overcome this challenge, people need an effective tool to highlight and separate the necessary contents from infinite amount of information, and to personalize and structure the necessary contents to generate a personal database so that information can be retrieved quickly in the future.

In related art, content providers collect information from the world and structure the information in various fixed formats such as videos, images, or other forms, and then deliver the multimedia content to the users. However, the users may not be able to highlight and separate the necessary contents from the fixed format information provided by the content providers. Therefore, the users may not be able to highlight and save the necessary contents into their respective personal databases.

Research in the field of learning and memory reveals that people's knowledge mainly comes from acquiring and retaining visual and audio information about the world they live in. A person can naturally acquire and retain a very short episode of new visual and audio information in his or her short-term memory. If the person did not pay attention and/or had an emotion above a predetermined threshold with respect to this information, the information decays in just a few seconds and disappears from the person's memory.

To solve the above problem, in today's learning environment, students use cameras to record their lectures during various classroom sessions. Students can also take notes in their notebooks with respect to the observed material. At home, they may playback the videos and then use the notes to develop learning comprehension. In related art, this method takes time and efforts but the results may be unsatisfactory or insufficient for various reasons.

For example, it is not easy to navigate to the necessary contents inside the video and it may be impossible to create the links between the notes and the respective necessary contents inside the video. In addition, it is impossible to link further notes, comments, and enriched contents into the necessary contents inside the video. Because different necessary contents may be located at different locations throughout the video, establishing links between them is also difficult. The video, in turn, is not easy to link into the individual's cognitive database.

As a consequence, significant time and efforts may be invested but learning comprehension of the material may still be poor and the needed information may not be retained by the user. Accordingly, there is a need in the art to provide a system that would enhance learning comprehension of various materials.

The above information is presented as background to a state of the computerized arts and only to assist with understanding of the present disclosure. No determination has been made, and no assertions are made that any of the above descriptions are applicable as prior art with regard to the present disclosure. The information presented only describes related art techniques, which could be techniques based on an internal knowledge of the Applicant.

SUMMARY

In one or more exemplary embodiments, a computerized system is provided. The system generates a user sensory reference timeline. Then, based on this reference timeline, the system breaks down the contents into various blocks and generates cues therein between the various blocks.

In one or more exemplary embodiments, a computerized system that mimics a human mind is provided, to learn information of each sensory data block, to generate episodic data block, and semantic data block for each sensory data block.

In one or more exemplary embodiments, a computerized system is provided, which receives input from user and allows the user to interact directly with the key contents, thereby helping the user comprehend the contents.

In one or more exemplary embodiments, a computerized system is provided, which organizes these comprehensive contents into their personal lifetime database for the effective recalls and uses in the future.

In one or more exemplary embodiments, a computerized system is provided, which builds a cognitive map and tools for an effective finding of a particular contents in a user's personal cognitive database is provided.

In one or more exemplary embodiments, cognitive content network is built to link, connect, and exchange the cognitive content from this individual's cognitive content database to others, connecting people in a more efficient and harmonious way.

Illustrative, non-limiting embodiments may overcome the above disadvantages and other disadvantages not described above, and also may have been developed to provide solutions to other disadvantages and problems that were not described above. However, a method, an apparatus, a system, and a computer readable medium that operates according to the teachings of the present disclosure are not necessarily required to overcome any of the particular problems or disadvantages described above. It is understood that one or more exemplary embodiment is not required to overcome the disadvantages described above, and may not overcome any of the problems described above. The appended claims should be consulted to ascertain the true scope of the present disclosure.

According to an aspect of various exemplary, non-limiting embodiments, a computerized method is provided. The method provides individualized, cognitive assistance and includes receiving, by a computer, data of a user comprising visual and audio information, a corresponding time information and a corresponding location information. The method further includes generating, by the computer, at least one timeline related to a time period in which the data was obtained by the user and generating and stamping, on the at least one timeline, a plurality of consecutive episodic reference timepoints, which are spaced apart equidistant from one another. The method further includes dividing the data into a plurality of consecutive sensory data blocks. The plurality of consecutive sensory data blocks are the same predetermined size and each of the plurality of consecutive sensory data blocks includes one reference timepoint from among the plurality of consecutive episodic reference timepoints. The method further includes generating a semantic data block for each of the plurality of consecutive sensory data blocks. Each semantic data block includes at least one semantic cue related to a meaning of content of the respective sensory data block. The method also includes stamping the reference timepoint of the respective sensory data block onto the respective semantic data block and displaying, in a first area of a display of the computer, the plurality of consecutive sensory data blocks and in a second area of the display, a corresponding plurality of semantic data blocks that are synchronized with the plurality of consecutive sensory data block based on the stamped reference timepoint.

According to various exemplary, non-limiting embodiments, the method may further include generating an episodic data block for each of the plurality of consecutive sensory data blocks. The episodic data block may include at least one episodic cue generated by simplifying a plurality of images of the visual information of the respective sensory data block from among the plurality of consecutive sensory data blocks. The method may further include stamping the reference timepoint of the respective sensory data block onto the respective episodic data block and displaying a plurality of consecutive episodic data blocks in the first area of the display synchronized with the corresponding plurality semantic data blocks in the second area of the display, based on the stamped reference timepoint. The at least one semantic cue of the semantic data block might be at least one of a blank, a text, a symbol, a flashing dot, and a color-coded highlight.

According to various exemplary, non-limiting embodiments, the method may further include receiving, via a user input interface of the computer, input from the user. The input may include the at least one semantic cue. The method may further include generating the at least one semantic cue of said each semantic data block which is the at least one of the blank, the text, the symbol, the flashing dot, and the color highlight, based on at least one semantic analysis of the respective sensory data block and based on the user input.

According to various exemplary, non-limiting embodiments, the method may further include receiving additional input from the user. The input may include a first selection of a position of a navigation start indicating a starting reference timepoint on the at least one timeline and a second selection of a forward navigation or a backward navigation. The method may further include consecutively displaying a plurality of consecutive positions of consecutive reference timepoints starting from the starting reference timepoint on the second area of the display, and the respective plurality of the consecutive semantic blocks in the second area of the display in synchronization with the respective plurality of consecutive episodic block in the first area of the display.

According to various exemplary, non-limiting embodiments, the method may further include receiving, via a user interface of the computer, an input from the user that includes at least one semantic cue. The method may further include searching a plurality of consecutive semantic data blocks to find one semantic data block that includes the semantic cue input by the user. The method may also include displaying, in the second area of the display, a first found semantic data block based on the searching and displaying, in the first area of the display, the respective episodic data block in synchronization with the first found semantic data block.

According to various exemplary, non-limiting embodiments, the method may further include receiving an additional input from the user including one of a confirmation of the first found semantic data block or a rejection of the first found semantic data block. Based on the additional input including the confirmation of the one semantic data block, the method may further include consecutively displaying a plurality of consecutive semantic data blocks starting from at least one first semantic data block preceding the first found semantic data block and until receiving additional input to end the displaying and consecutively displaying, in the first area of the display, a respective plurality of consecutive sensory data blocks in synchronization with the plurality of the displayed consecutive semantic data blocks. Based on the additional input including the rejection of the first found semantic data block, the method may further include continue searching in succeeding plurality of semantic data blocks to find a next found semantic data block including the semantic cue input by the user and displaying the next found semantic data block in the second area of the display and the respective episodic data block in the first area of the display in synchronization with the next found semantic data block.

According to various exemplary, non-limiting embodiments, the method may further include displaying on a third area of the display the at least one timeline which includes a first timeline and a second timeline. The first timeline includes the plurality of consecutive reference timepoints which are linked with the plurality of the respective sensory data blocks. The second timeline includes a set of consecutive reference timepoints from among the plurality of consecutive reference timepoints that are linked to a set of sensory data blocks from among the plurality of the consecutive sensory data blocks. The set of sensory data blocks have been viewed at least once before by the user.

According to various exemplary, non-limiting embodiments, the method may further include receiving an input from the user which includes a selection of a key semantic data block from among the plurality of semantic data blocks. The selected key semantic data block includes content defined by the user as useful and needed for future. The method further includes displaying a flashing dot indicating a location of the reference time point of the key semantic data block on the first timeline.

According to various exemplary, non-limiting embodiments, the method may further include receiving an input from the user including a first selection of a first semantic data block from among the plurality of semantic data blocks and a second selection of a second semantic data block from among the plurality of semantic data blocks. The first semantic data block is a starting semantic data block and the second semantic data block is an ending semantic data block of a plurality of consecutive semantic data blocks that include contents defined by the user as useful and needed for future. The method may further include displaying, on the second timeline, a set of reference timepoints from a first location of the first semantic data block to a second location of the second semantic data block in a single color coded highlighted data block.

According to various exemplary, non-limiting embodiments, the method may further include receiving input from the user that includes a first selection of a position of a navigation start which is a first flashing dot from among a plurality of flashing dots, determining a first reference timepoint of the first flashing dot, and displaying the determined first reference timepoint of the first flashing dot and a respective first semantic data block corresponding to the determined first reference timepoint in the second area of the display and a respective first episodic data block in synchronization with the determined first reference timepoint in the first area of the display.

According to various exemplary, non-limiting embodiments, the method may further include receiving an additional input from the user including one of a confirmation of the first flashing dot or a rejection of the first flashing dot. Based on the additional input being the confirmation of the first flashing dot, the method may further include consecutively displaying, in the second area of the display, a set of consecutive semantic data blocks from among a plurality of consecutive semantic data blocks starting from at least one second semantic data block preceding the first reference timepoint until receiving additional input to end the displaying and consecutively displaying, in the first area of the display, a set of consecutive sensory data blocks corresponding to and in synchronization with the set of consecutive semantic data blocks. Based on the additional input being the rejection of the first flashing dot, the method may further include navigating to a next flashing dot from among the plurality of flashing dots, determining a next reference timepoint, and displaying a next semantic data block corresponding to the next reference timepoint in the second area of the display and the respective episodic data block in the first area of the display in synchronization with the next semantic data block.

According to various exemplary, non-limiting embodiments, the method may further include receiving input from the user including a selection of a position of a navigation start indicated with a first color coded highlighted portion in the second timeline, determining a first starting reference timepoint of a first starting semantic data block of the first color coded highlighted portion corresponding to the selection, and displaying the determined first starting reference timepoint and a first starting semantic data block in the second area of the display and a first starting episodic data block corresponding to and in synchronization with the determined first starting reference timepoint in the first area of the display.

According to various exemplary, non-limiting embodiments, the method may further include receiving an additional input from the user including a confirmation of the first color coded highlighted portion or a rejection of the first color coded highlighted portion. Based on the additional input indicating the confirmation of the first color coded highlighted portion, the method may further include consecutively displaying a set of consecutive semantic data blocks starting from the first starting reference timepoint and ending at an ending reference timepoint of consecutive color coded highlighted data blocks in the second area of the display and consecutively displaying, in the first area of the display, a respective set of consecutive sensory data blocks corresponding to and in synchronization with the set of consecutive semantic data blocks. Based on the additional input indicating the rejection of the first color coded highlighted portion, the method may further include moving to a next color coded highlighted portion, determining a next starting reference timepoint of the next color coded highlight portion, and displaying the next starting reference timepoint and next starting semantic data block corresponding to the next starting reference timepoint in the second area of the display and next starting episodic data block corresponding to and in synchronization with the next starting reference timepoint in the first area of the display.

According to various exemplary, non-limiting embodiments, the data of the user is sensory data captured from the user by an apparatus. The sensory data includes an environment observed by a user and a cognitive state of the user with respect to the environment.

According to various exemplary, non-limiting embodiments, the data of the user is at least one of communication data obtained from the user communicating with another entity via a network or data downloaded from the network.

According to various exemplary, non-limiting embodiments, the data of the user includes at least one of: first data which is sensory data obtained from a first source and the visual and audio information of the sensory data includes an environment observed by the user, or second data obtained from a second source different from the first source, the second source including multimedia data being downloaded via a network.

According to another aspect of various exemplary embodiments, an apparatus is provided. The apparatus is for providing individualized cognitive assistance and includes a memory configured to store computer executable instructions and a processor configured to execute the stored computer executable instructions. When the instructions are executed by the processor, they cause the processor to receive data of a user including visual and audio information, a corresponding time information, and a corresponding location information, generate at least one timeline related to a time period in which the data was obtained by the user, and generate and stamp, on the at least one timeline, a plurality of consecutive episodic reference timepoints, which are spaced apart equidistant from one another. These instructions further cause the processor to divide the data into a plurality of consecutive sensory data blocks. The plurality of consecutive sensory data blocks are of the same predetermined size. Each of the plurality of consecutive sensory data blocks include one reference timepoint from among the plurality of consecutive episodic reference timepoints. These instructions further cause the processor to generate a semantic data block for each of the plurality of consecutive sensory data blocks. Each semantic data block includes at least one semantic cue related to a meaning of content of the respective sensory data block. The reference timepoint of the respective sensory data block is stamped onto the respective semantic data block. These instructions further cause the processor to control a display to display in a first area of, the plurality of consecutive sensory data blocks and in a second area, a corresponding plurality of semantic data blocks that are synchronized with the plurality of consecutive sensory data block based on the stamped reference timepoint.

According to various exemplary, non-limiting embodiments, the stored computer executable instructions may further cause the processor to generate an episodic data block for each of the plurality of consecutive sensory data blocks. The episodic data block may include at least one episodic cue generated by simplifying a plurality of images of the visual information of the respective sensory data block from among the plurality of consecutive sensory data blocks. The stored computer executable instructions may further cause the processor to stamp the reference timepoint of the respective sensory data block onto the respective episodic data block and control the display to display a plurality of consecutive episodic data blocks in the first area synchronized with the corresponding plurality semantic data blocks in the second area, based on the stamped reference timepoint. The at least one semantic cue of the semantic data block is at least one of a blank, a text, a symbol, a flashing dot, and a color-coded highlight.

According to various exemplary, non-limiting embodiments, the apparatus may further include a user interface configured to receive an input from the user including at least one semantic cue. The stored computer executable instructions may further cause the processor to search a plurality of consecutive semantic data blocks to find one semantic data block including the semantic cue input by the user and control the display to display, in the second area of the display, a first found semantic data block based on the searching and to display, in the first area of the display, the respective episodic data block in synchronization with the first found semantic data block.

According to yet another aspect of various exemplary embodiments, a method is provided. The method provides individualized cognitive assistance and includes receiving sensory data of a user that includes visual and audio information observed by the user from an environment or obtained from communicating with another user via a network, a corresponding time and location information. The method further includes generating a plurality of cues for the received sensory data. The cues include at least one of a semantic meaning of the visual and audio information. The semantic meaning is obtained based on a user input. The method may further include storing the received sensory data in a personal cognitive database, which is structured based on the generated plurality of cues such that portions of the sensory data are linked together based on the cues and selectively displaying at least the portions of the sensory data that are linked together based on the cues.

BRIEF DESCRIPTION OF THE DRAWINGS

The accompanying drawings, which are incorporated in and constitute a part of this specification exemplify embodiments and, together with the description, serve to explain and illustrate exemplary embodiments. Specifically.

DETAILED DESCRIPTION OF EXEMPLARY EMBODIMENTS

Exemplary embodiments will now be described in detail with reference to the accompanying drawings. Exemplary embodiments may be embodied in many different forms and should not be construed as being limited to the illustrative exemplary embodiments set forth herein. Rather, the exemplary embodiments are provided so that this disclosure will be thorough and complete, and will fully convey the illustrative concept to those skilled in the art. Also, well-known functions or constructions may be omitted to provide a clear and concise description of exemplary embodiments. The claims and their equivalents should be consulted to ascertain the true scope of an inventive concept.

The descriptions of the various exemplary embodiments have been presented for purposes of illustration, but are not intended to be exhaustive or limited to the embodiments disclosed.

Figure 1:
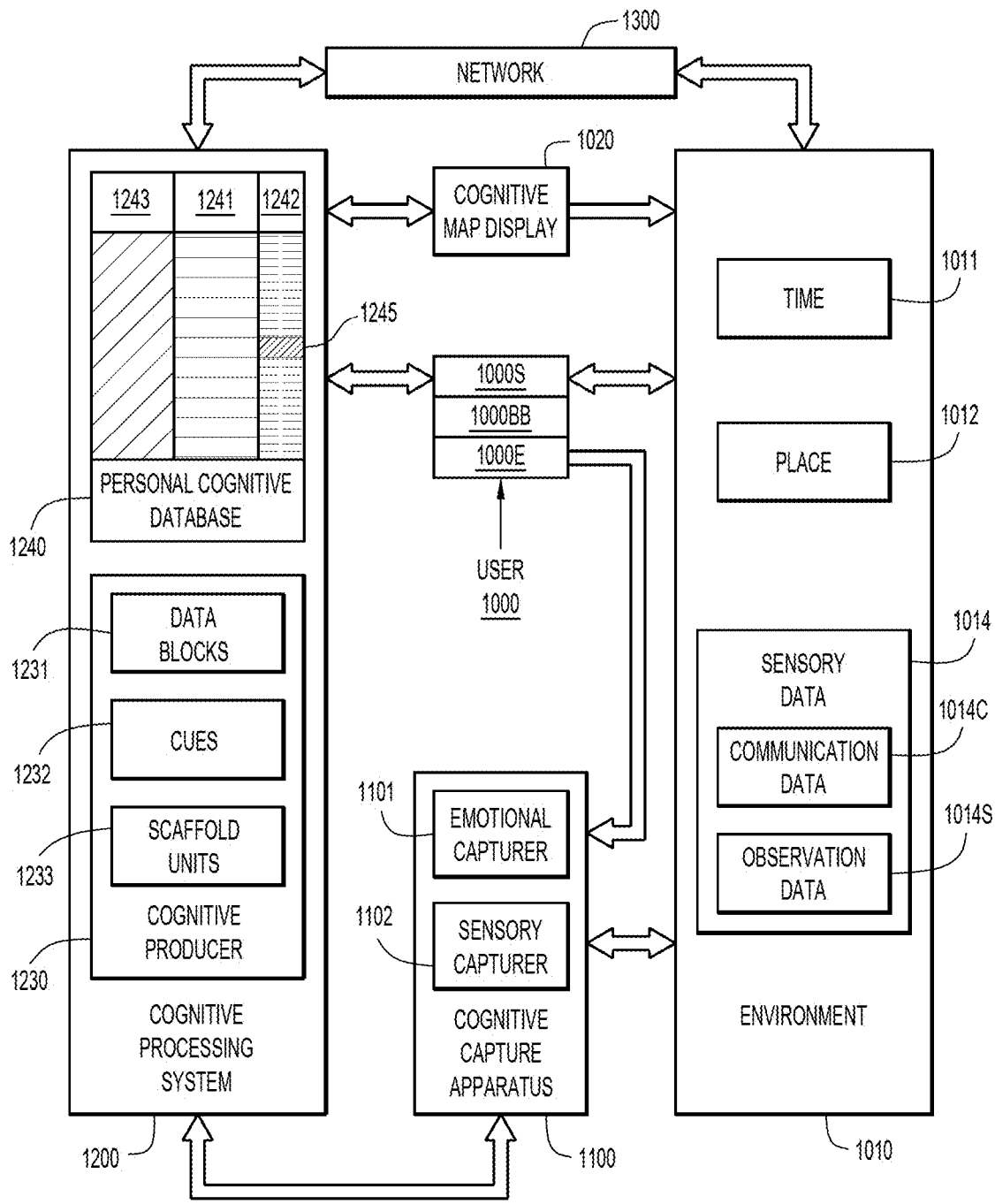
FIG. 1 is a block diagram illustrating a computerized cognitive assistant system, according to an exemplary embodiment.

FIG. 1 is a block diagram illustrating a computerized cognitive assistant system to build a personal cognitive database, according to an exemplary embodiment. In FIG. 1, the cognitive assistance system includes a cognitive capture apparatus 1100, a cognitive processing system 1200, and a cognitive map display 1020. The cognitive capture apparatus captures signals from the user 1000 and an environment 1010 of the user 1000.

As illustrated in FIG. 1, the user 1000 has a brain and a body (collectively shown as 1000BB) and different organs which receive sensory data 1014 from the environment 1010 and generate user's response data 1000S under semantic forms such as audio (utterances made by the user 1000), gestures, and actions to communicate and interact with the system, other people, and the environment 1010. For example and not by way of a limitation, the user 1000 can speak into a microphone to execute a voice command, type the command on a keyboard, touch a touch screen to enter the command or an instruction into the system. The user may also use gestures to interact with the system.

The brain and body (including different organs) 1000BB of the user 1000 and generate emotional data or user's cognitive emotional state 1000E, which provide feedback about the statuses of the user's brain and body 1000BB at each point of time. For example and not by way of a limitation, the bandwidth of brainwave may change, the heartbeat of the user may increase, the blood pressure may increase, and the pupils may become dilated. As another example and not by way of a limitation, the user may unintentionally shake his head or tap his foot.

According to an exemplary embodiment, the cognitive capture apparatus 1100 includes an emotional capturer 1101 (cognitive state capturer) and a sensory capturer 1102.

The emotional capturer 1101 is worn by the user 1000 and captures user's emotional data generated by the different organs and the brain and body 1000BB of the user 1000. It may be a cognitive headset with an EEG sensor to capture brainwave data, it may be a device worn on a finger of the user which captures emotional data of the user 1000, according to various exemplary embodiments. The emotional capturer 1101 may capture emotional data of the user 1000 through physiological signals by measuring Heart Rate (HR), by way of an example.

According to an exemplary embodiment, the emotional capturer 1101 may include another device worn on a hand of the user 1000 similar to a watch or a bracelet to capture emotional data of the user 1000. The emotional capturer 1101 may capture emotional data of the user through physiological signals by measuring blood volume pulse (BVP) and skin temperature (SKT), by way of an example and not by way of a limitation. The emotional capturer 1101 is described in further detail below with reference to FIGS. 2A-3B.

According to an exemplary embodiment, the emotional capturer 1101 may include other devices such as a microphone to capture user's emotional data under the forms of semantic voice, a key board or a touch screen to capture user's emotional data under the forms of actions (typing, touching) or gestures (swiping, tapping).

The emotional capturer 1101 captures an internal, episodic cognitive state of the user 1000 based on signals generated by the user 1000.

The sensory capturer 1102 may be worn by a user 1000 as a headset or a camera to capture observation data in the surrounding environment that may be seen and heard directly by the user 1000, according to an exemplary embodiment. The sensory capturer 1102 may be carried by a user such as a smart phone to capture communication data in a telecommunication, according to various exemplary embodiments. The sensory capturer 1102 is an external episodic cognitive capturer because it captures user's surrounding, external data or environment observed by the user.

The environment 1010 captured by the cognitive capture apparatus 1100 includes time information or time component (time 1011) and place information or place component (place 1012) and data observed by the user i.e., the sensory data 1014. The sensory data 1014 includes communication data 1014C when the user 1000 is receiving data from other entities (other communication devices) through direct communication and telecommunication, and observation data 1014S when the user is receiving data from environment through observations. In one example embodiment, the observation data 1014S may include data downloaded from the network such as the internet.

The cognitive processing system 1200 includes a cognitive producer 1230 and a personal cognitive database 1240. The cognitive processing system 1200 includes at least one hardware processor and a memory which stores instructions to be executed by the processor. The processor may load a command or data received from another component of the cognitive assistant system such as from the cognitive capture apparatus 1100. The command may contain a code that is generated by a compiler to be executable by the processor.

The sensory data captured by cognitive capture apparatus 1100 is transferred to cognitive processing system 1200 via network 1300 (which may include one or more networks such as a data network (Internet), local access network (LAN), and so on). In the cognitive processing system 1200, the cognitive producer 1230 generates at least one timeline, which has a plurality of consecutive real-timepoints . . . t−1, t, t+1, t+2 . . . of lifetime of the user. The cognitive producer 1230 also generates and stamps consecutive reference timepoints on the generated timeline of the user, where the timespan between two consecutive reference timepoints is identical. Then the cognitive producer 1230 divides the sensory data 1241 into a plurality of consecutive sensory data blocks 1231(1), 1231(2), 1231(3) . . . 1231(n) (data blocks 1231). The sensory data 1241 is divided based on the generated consecutive reference timepoints of the generated timeline. The length of a sensory data block is identical and equal to the timespan between two consecutive reference timepoints on the generated timeline of the user which is also determined based on the necessary time that a person uses to speak an average-length meaning with an average speed according to an exemplary embodiment. The length may be from 2 seconds to 3 seconds. The length may be 2.16 seconds which may be the exact basic individual natural cycle of human's cognitive processes. The length may be 2 seconds which may be the nearest whole number to the basic individual natural cycle of human's cognitive processes.

The cognitive producer 1230 further generates a unique block address for each sensory data block based on one of time points on the each sensory data block.

The cognitive producer 1230 further analyzes each of the sensory data blocks (data blocks 1231) to generate episodic data blocks (cues 1232) and semantic data blocks (scaffold units 1233), described in further detail below, according to various exemplary embodiments.

An episodic data block represents the context of the respective sensory data block which includes an image cue, a time cue, and place cue. The episodic data block may also include additional cues such as an emotional state of the user. In an example embodiment, scenic, emotional, place, and time (SEPT) cues may be represented by an episodic data block. In another exemplary embodiment, the emotional state of the user may be part of semantic cues and a semantic block explained in further detail below.

A scenic cue may be an image generated from a number of images within the respective sensory data block. For example, if the length of sensory data block is two seconds, the number of images within that sensory data block may be 60 images. The system captures or obtains one image from the sixty images and then further simplifies this image to illustrate a cue which then represents the sixty other images. This solution minimizes the use of memory and speeds up the navigation during a recall process.

A time cue relates to the time when the respective episodic cognitive data block occurred and was downloaded by the user from the network. The time cue may be the unique block address for each sensory data block which is identified based on the clock of the devices, and which is synced with a world clock, for example such as 08:01:02 AM Eastern Time, Feb. 6, 2019. The time cue of a sensory data block may be identified by one of time start of a respective sensory data block from among the plurality of sensory data blocks or time end of the respective sensory data block from among the plurality of sensory data blocks or a time point between the time start and/or the time end of the respective sensory data block such as at the mid-point of that sensory data block. These are provided by way of an example and not by way of a limitation.

A place cue is where the user was living with, during the said sensory data block was happening, for example such as MIT lab, Cambridge, Mass., USA and where the user was downloading the said sensory data such as home, office, library and so on.

According to an exemplary embodiment, based on the cues 1232, semantic data blocks (scaffold units 1233) are generated. The semantic data blocks include semantic cues which represent the key contents and/or the key meaning of that sensory data block. A semantic cue may be text, symbol, and/or color mark. Semantic cues are obtained using semantic analysis, which may include interpreting from the content of the respective sensory data block, and representing the key information of the sensory data block. Semantic cues may be in the linguistic forms which are most compatible with a human's mind and human's natural ability to recall. According to an exemplary embodiment, the semantic cues of a sensory data block include text interpreted from the voice and/or image moving within that said sensory data block. According to another exemplary embodiment, the semantic cues of a sensory data block include text, symbols, color codes, and so on input by the user and/or interpreted from the user's emotional data.

Additionally, the scaffold units 1233 may include links to other additional contents that the user and users add (enriched contents). The enriched contents may be videos or photos captured by friends (multimedia contents). It may be pdf or jpeg format files downloaded from Internet. It may be a text file or a definition downloaded from an Internet. In an exemplary embodiment, the enriched contents is contents from an external source linked to at least one sensory data block. The cognitive producer 1230 further stamps block address on each respective block and links respective blocks into user timeline to build user's personal cognitive database 1240.

The cognitive processing system 1200 also includes a personal cognitive database 1240. The personal cognitive database 1240 includes a sensory database 1241, a cued episodic database 1242, a cued semantic database 1243 (and may also include an enriched database, not shown), and a navigator 1245.

The sensory database 1241 includes all or at least some of the sensory data blocks that the user captures during his or her lifetime. It includes real-observation videos and photos along his or her lifetime including real-time viewing videos, photos, and other contents on user's screen computer. According to an exemplary embodiment, the sensory database 1241 may be stored on a cloud-based memory and is downloaded to a computer or a mobile device of a user and may store all types of multimedia data.

The episodic cued database 1242 includes a plurality of episodic data blocks (cues 1232(1), 1232(2) . . . 1232(n)), which are generated by the cognitive producer 1230 (cues 1232). According to an exemplary embodiment, the episodic cued database 1242 includes episodic data blocks (cues 1232) such as a plurality of episodic simplified images (Img1), (Img2), . . . , (Img n), which are generated by the cognitive producer 1230. In an exemplary embodiment, the episodic cued database 1242 may store location, scene, and a time for a respective sensory block but this is provided by way of an example and not by way of a limiting. According to an exemplary embodiment, the episodic cued database 1242 or a part of episodic cued database 1242 is stored on a user's computer or user's mobile device for quick search, recall and/or retrieval.

According to an exemplary embodiment, the semantic cued database or the semantic database 1243 includes a plurality of semantic data block 1233(1), 1233(2) . . . 1233(n), which are generated by cognitive producer 1230 and shown as scaffold units 1233 in FIG. 1. The semantic data block includes semantic cues about the content of its respective sensory data block, and may include a text, a symbol, a blank, obtained from voice to text conversion, image moving conversion or inputs from the users. In an exemplary embodiment, the cognitive producer 1230 performs semantic analysis to obtain meaning from a respective semantic block.

For example, based on semantic analysis of a respective sensory data block, the cognitive producer 1230 may determine that the block is about the brain and add brain as a semantic cue. Additionally, the cognitive producer 1230 may determine synonyms for the word "brain" and add synonyms as additional semantic cues. In an exemplary embodiment, semantic analysis may include: (1) converting multimedia data of a respective sensory data block to text and images, (2a) parsing the text to determine meaning or context of the sensory data block and (2b) performing image recognition to determine context of the images, and (3) generating at least one cue based on 2a and/or 2b. Since semantic analysis (or context analysis) is known in an art, detailed description is omitted so as not to obscure exemplary embodiments with an unnecessary detail. It is noted, however, that machine learning (ML) algorithms may be employed to determine context of a respective sensory data block. Additionally, neighboring sensory data blocks may be examined to determine context of the current sensory data block.

Additionally, a cognitive state of the user during the capture of the sensory data block and/or during the review of the sensory data block is detected by the emotional capturer 1101 and is added as a semantic cue to the semantic data block.

According to an exemplary embodiment, the sematic database 1243 or a larger part of sematic database 1243 may be stored on the user's computer or the user's mobile device for a quick navigation.

The enriched database (not shown) includes different data related to cued data. The enriched data is the data which is not real-time observed and is not captured by the user from the environment. It may be videos or photos captured by friends or the user at a different time and linked to the sensory data. Also, it may be notes taken by the user and/or other users that correspond to the captured environment.

The navigator 1245 is configured to move or traverse along the user's timeline or a portion of the timeline stored in the personal cognitive database 1240 to identify a semantic data block (from the semantic database 1243), a respective episodic data block (from the episodic cued database 1242), a respective sensory data block (from the sensory database 1241), and neighboring data blocks. The navigator 1245 is configured to display the identified semantic data block on a second area of the display (referred to as the cognitive map display 1020 in FIG. 1), the respective episodic data block on a first area of the display, and the user's timeline in a third area of the display.

When the cognitive processing system 1200 receives a request from the user 1000, the cognitive processing system 1200 may control the navigator 1245 to identify a relevant semantic data block based on the request and control the display to display the identified semantic data block and the respective episodic data block on the cognitive map display 1020.

According to various exemplary embodiments, the display is provided to display semantic data blocks, episodic data blocks, sensory data blocks, enriched data, and a map in a form of at least one timeline to help the user visibly identify the position of a cue or cues located in the user's cognitive database (on a user's personal timeline).

According to various exemplary embodiments, the sensory data blocks are displayed on the first area of the display. If the user wants to only play a video without taking or viewing notes, the processing system 1200 may control the display to display consecutive sensory data blocks on full area of the display.

According to various exemplary embodiments, an episodic data block is displayed on the first area of the display together with the respective semantic data block on the second area of the display and the timeline may be displayed at the middle of the two blocks. This is provided by way of an example and not by way of a limitation. One of ordinary skill in the art would readily appreciate that an episodic data block may be displayed together with a sensory data block, semantic data block, enriched data, one timeline, two timelines, and so on. The partition of the display, type of blocks, and the number of personal timelines, displayed will depend on a particular configuration or implementation of the system. Additionally, the partition of the display, type of blocks, and the number of personal timelines may be pre-configured by the user.

Figure 2A:
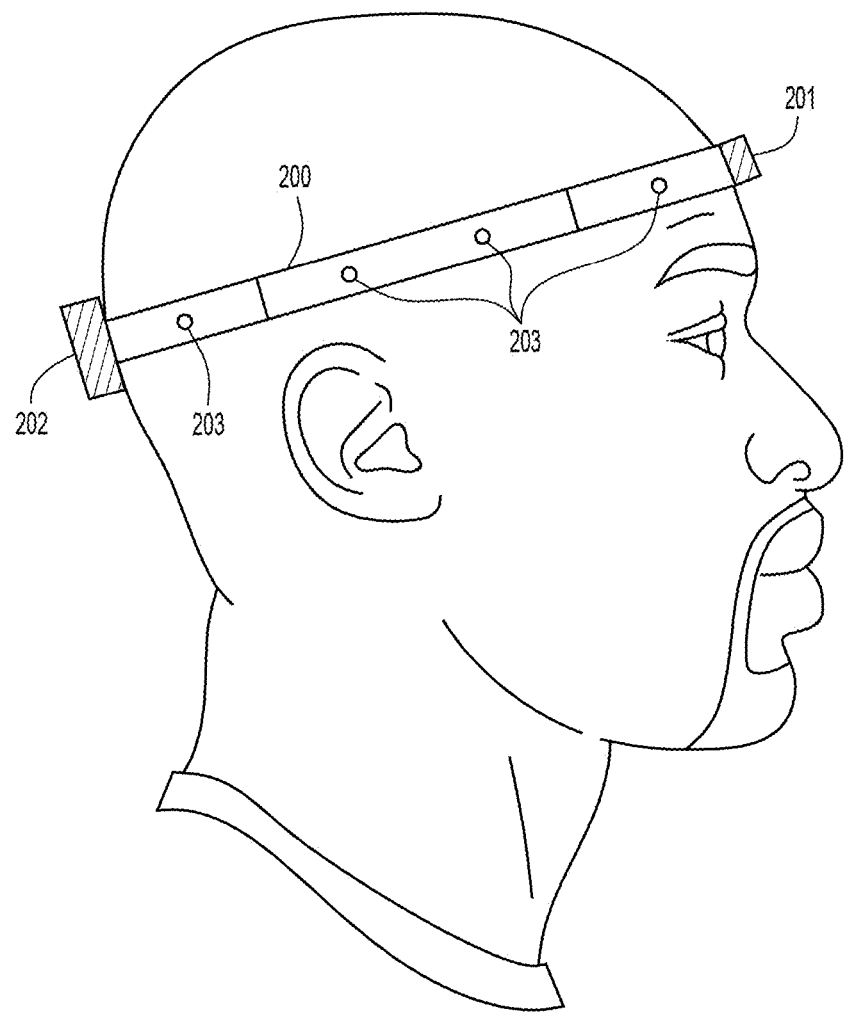
FIGS. 2A-2G are views illustrating a cognitive capture apparatus capturing sensory data through various direct observation and communication environments, according to various exemplary embodiments.

According to various exemplary embodiments, FIG. 2A is a block diagram illustrating a cognitive capture apparatus, according to an exemplary embodiment. The cognitive capture apparatus 200 is worn by a user as a headset. The cognitive capture apparatus 200 captures observation data and emotional data of the user. The apparatus is configured with sensors 203, a camera 201, and an electronic circuit board 202.

As illustrated in FIG. 2A, a camera 201 includes a microphone and may be provided on a front portion of the cognitive capture apparatus 200, according to an exemplary embodiment. This is provided by way of an example and not by way of a limitation. Multiple cameras may be provided such as a left camera, a front camera, a right camera, and a back camera to capture visual data and/or audio data according to an exemplary embodiment. One of ordinary skill in the art would readily appreciate that visual data and/or audio data may be captured with a personal device such as a user's personal data assistant or a cellular telephone. The captured visual and audio data (VI) may then be transferred to an electronic circuit board 202, which includes at least a memory coupled with a processor.

In an exemplary embodiment, the electronic circuit board 202 may process sensory data to generate cognitive and emotional state of a user. In yet another exemplary embodiment, the generated cognitive and emotional state information may be transmitted to another remote device such as the cognitive processing system 1200 (depicted in FIG. 1) for storage, monitoring, or further processing via a communication interface (not shown) provided on the cognitive capture apparatus 200. For example, the cognitive capture apparatus 200 may include a communication interface (e.g., a network card, an antenna, and other interfaces known to one of ordinary skill in the art or later developed) to transmit the data wirelessly e.g., a Bluetooth, Infrared, WiFi, and/or a cellular network to a remote server or a cloud for further storage, processing or monitoring and co-supervising. The communication interface may be built into the electronic circuit board 202, or may be provided as a separate device on the cognitive capture apparatus 200. According to an exemplary embodiment, a USB port may be provided on the electronic circuit board 202 or separately on the cognitive capture apparatus 200 so as to plug into a computer to transfer captured data.

In an exemplary embodiment, one or more sensors 203 (such as emotional sensors or cognitive state sensors) are further provided on the cognitive capture apparatus 200. While FIG. 2A depicts four cognitive state sensors 203, this is provided by way of an example and not by way of a limitation. One of ordinary skill in the art would readily appreciate that a single sensory or cognitive state sensor may be used but preferably multiple cognitive state sensors are provided to capture cognitive state of a user. The cognitive state sensors 203 may be provided on both sides of the headset. In an exemplary embodiment depicted in FIG. 2A, only one side of the user's head is shown but the other side may also include four cognitive state sensors 203 that detect the cognitive state of the user. That is, in an exemplary embodiment, cognitive state is obtained from multiple cognitive state sensors 203 by detecting activities in various parts of the brain.

For example, the U.S. Pat. No. 9,711,056 to Nguyen describes capturing, detecting, and identifying different types of emotional stimulation generated by human organs while the human is exploring and observing the environment, which is incorporated herein by reference for its helpful descriptions.

Additionally, the U.S. Pat. No. 10,127,825 to Nguyen, incorporated herein by reference for its helpful descriptions, describes assisting a user in learning, review, and memorization.

Also, the U.S. patent application Ser. No. 16/213,577 to Nguyen, filed on Dec. 7, 2018, incorporated herein by reference for its helpful descriptions, describes a communication apparatus which may capture communication data and cognitive data.

Figure 2B:
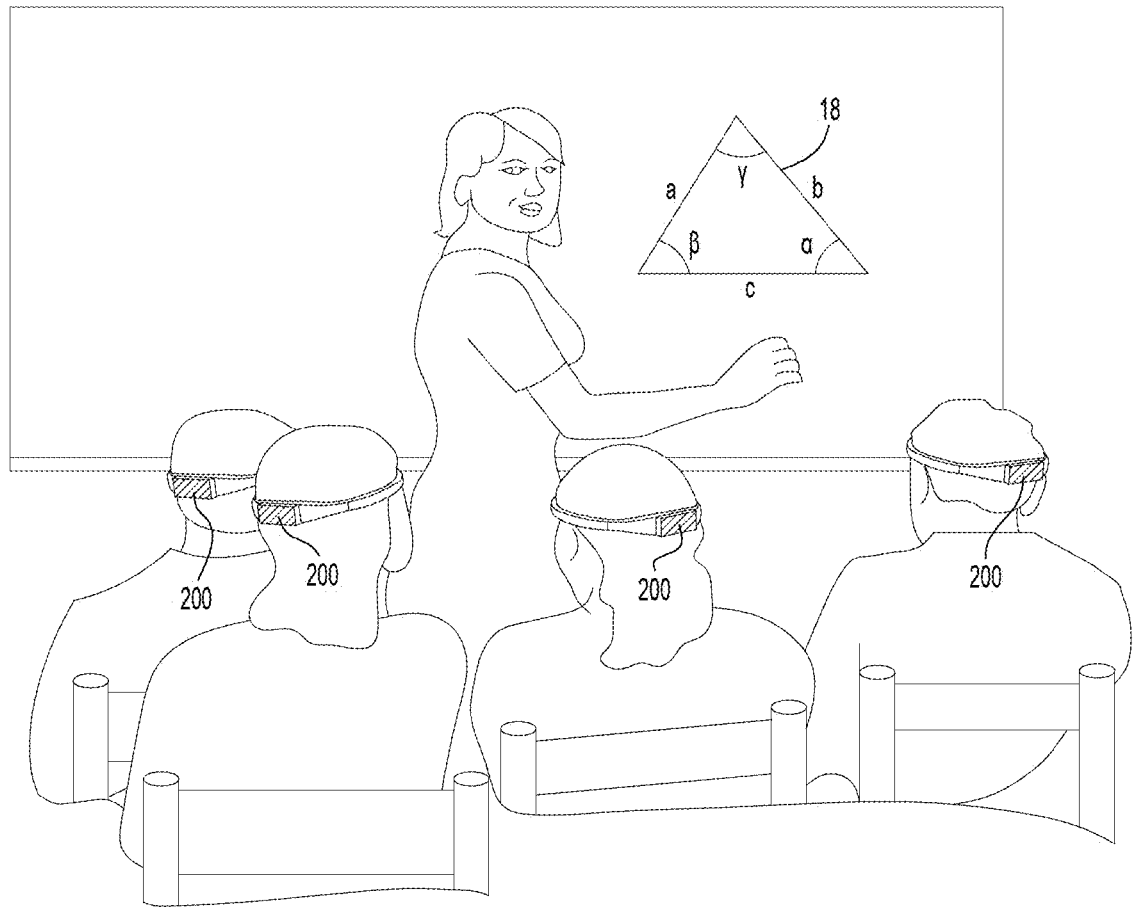
Figure 2C:
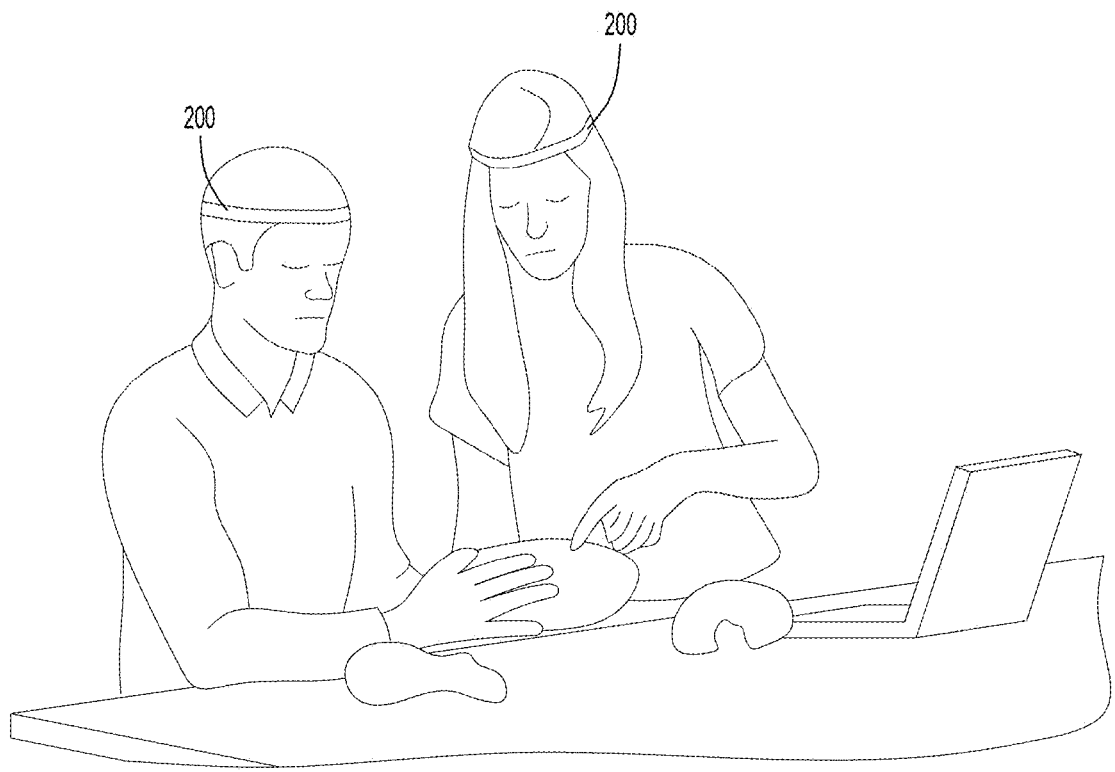
Figure 2D:
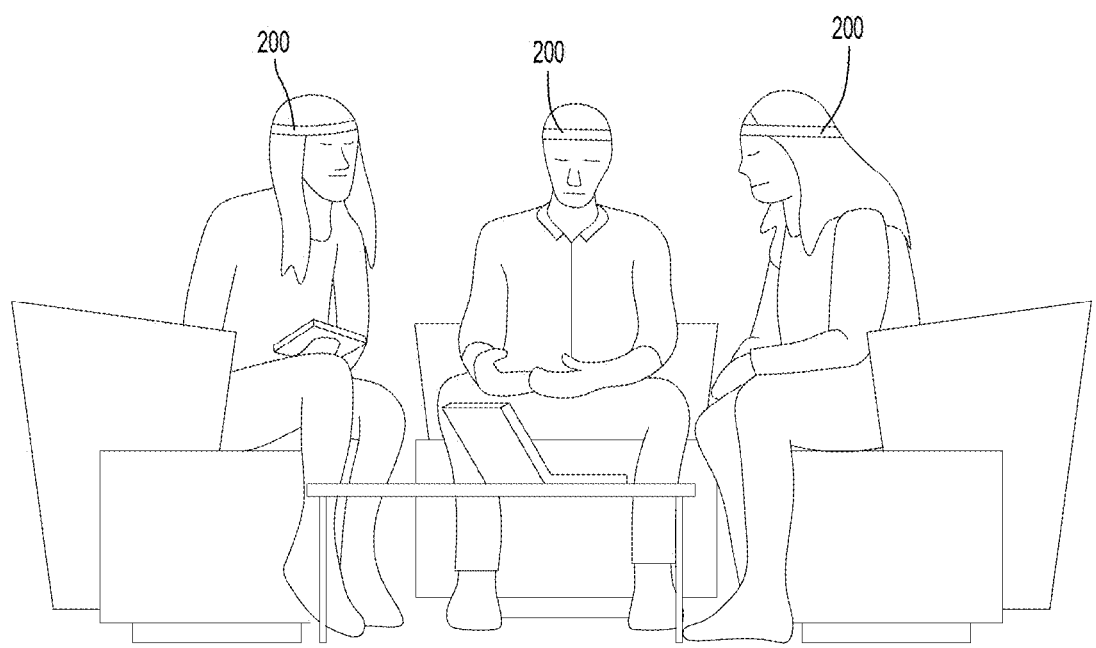
Figure 2E:
Figure 2F:
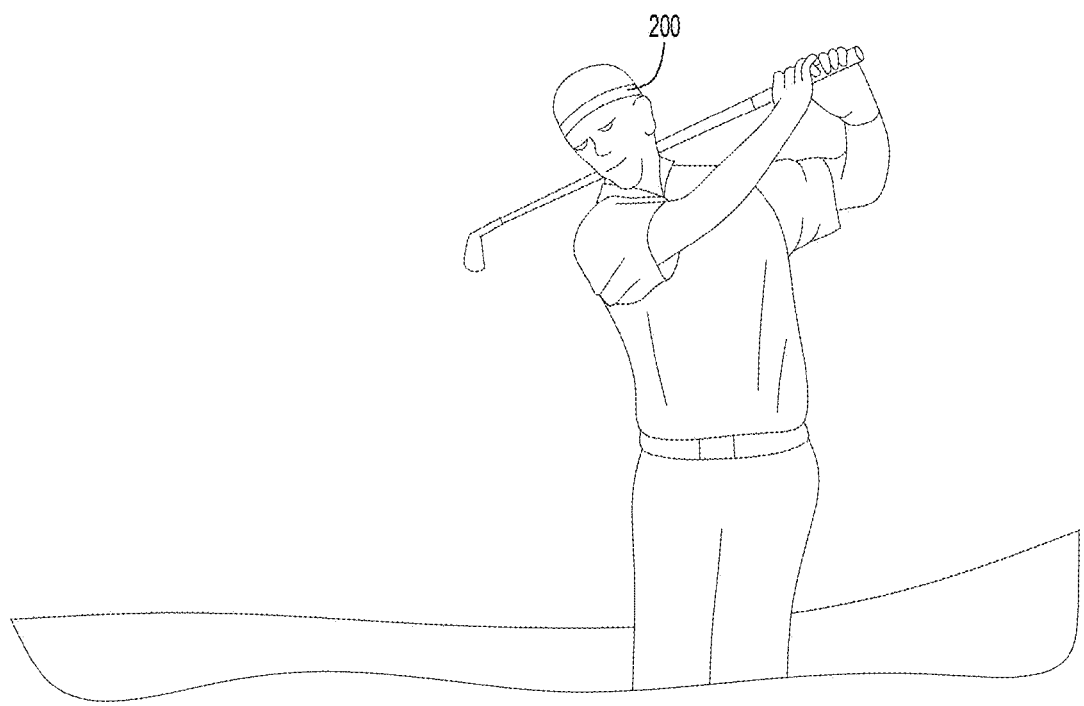
Figure 2G:

According to various exemplary embodiments, FIG. 2B is a view illustrating cognitive capture apparatus 200 being worn by users as students in a classroom to capture video lecture 18 presented by a professor. According to various exemplary embodiments, FIG. 2C is a view illustrating cognitive capture apparatus 200 being worn by users as students in a science laboratory to capture direct observations, communication data, and emotional data of the users. According to various exemplary embodiments, FIG. 2D is a view illustrating capture apparatus 200 being worn by users as students in a study group to capture direct discussions, communication data, and emotional data of the respective users. According to various exemplary embodiments, FIGS. 2E and 2F are views illustrating cognitive capture apparatus 200 being worn by users that are playing golf to capture observation data, motion data, and emotional data of the users. According to various exemplary embodiments, FIG. 2G is a view illustrating a cognitive capture apparatus 200 being worn by an inspector to capture observation data and emotional data of the inspector. FIGS. 2B-2G are views illustrating various practical applications of the cognitive capture apparatus 200 and variety of data that is captured by the cognitive capture apparatus.

Figure 3A:
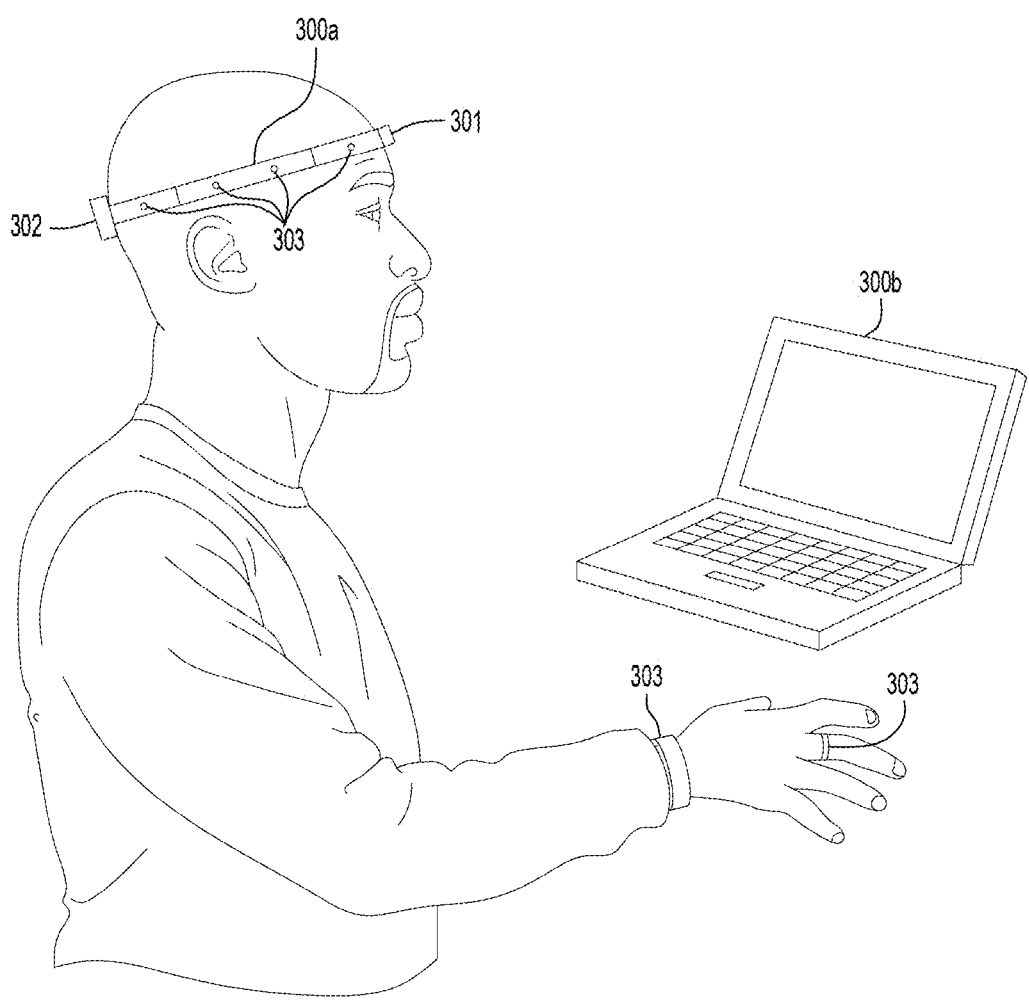
FIGS. 3A and 3B are views illustrating a cognitive capture apparatus capturing sensory data through various direct and indirect observation and communication environments, according to various exemplary embodiments.

According to various exemplary embodiments, FIG. 3A is view illustrating a cognitive capture apparatus 300a being worn by a user to capture direct observations, communication data, and emotional data, of the user. The apparatus 300a has a plurality of sensors 303 positioned all over the user's body including user's neck, various positions on his arms, fingers, and so on. The apparatus 300a also includes a camera 301 and an electronic circuit board 302. These features are analogous to the features described above with reference to FIG. 2A, accordingly detailed explanations is omitted for the sake of brevity. FIG. 3A also illustrates a cognitive apparatus 300b which is carried by a user to capture communications data such as tele-observation and tele-communication data of the user.

Figure 3B:
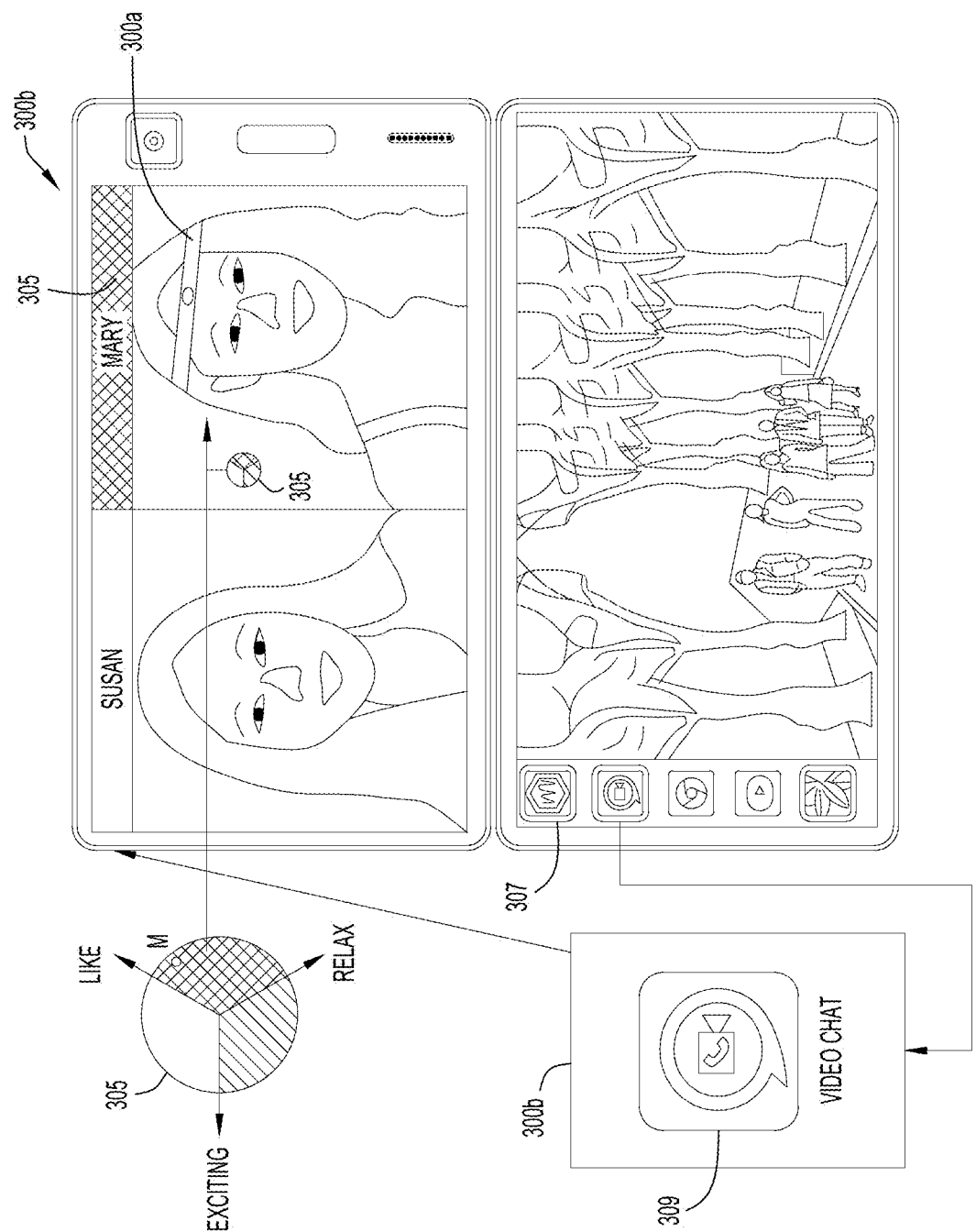

According to various exemplary embodiments, FIG. 3B is a view illustrating a cognitive apparatus 300b which is carried by a user to perform a live-streaming video conference call and capture tele-observation data and tele-communication data of the user and her friend. Further, cognitive state 305 of the user Mary may be captured and displayed via the cognitive apparatus 300*b*, when a sixth sense icon 307 is turned on to capture user's cognitive state. The cognitive apparatus 300*b* is displayed in a video chat mode 309.

Figure 4:
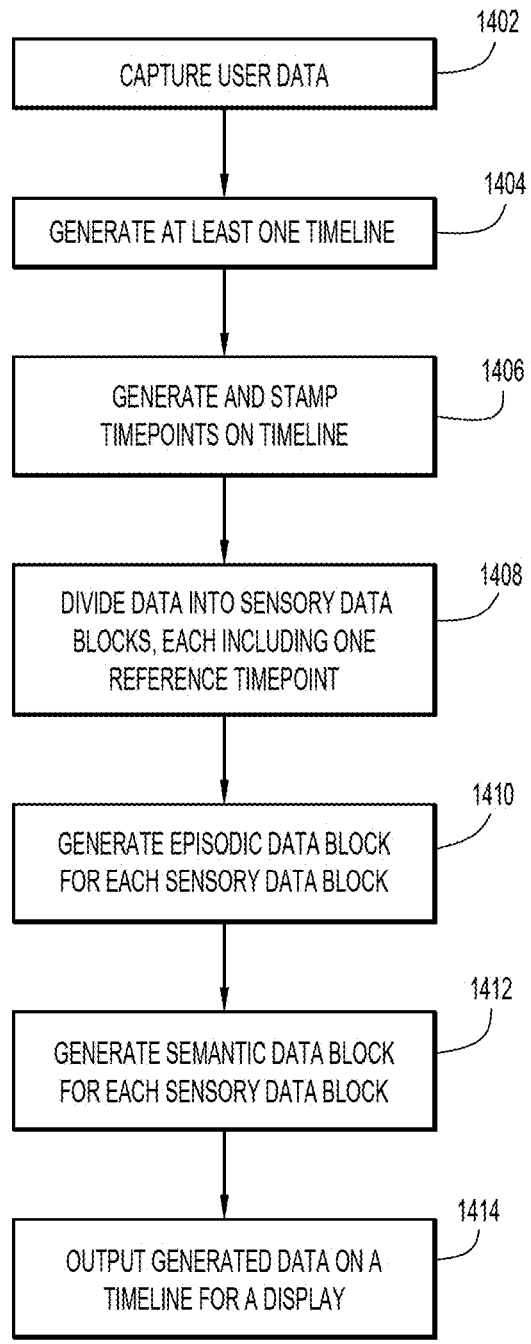
FIG. 4 is a flowchart illustrating a method of generating personal timeline, according to an exemplary embodiment.

FIG. 4 is a flowchart illustrating a method of generating personal timeline, according to an exemplary embodiment.

As illustrated in FIG. 4, in operation 1402, the cognitive capture apparatus 1100 (shown in FIG. 1) captures user data. The user data includes external user data obtained from the environment 1010 such as the time component (time 1011), the place component (place 1012), and sensory data 1014. The time information (time 1011) may be captured based on a clock provided in the cognitive capture apparatus 1100 or based on a connection with a tower, a server, and/or a satellite, as is known in the art. Accordingly, detailed description is omitted so as not to obscure the present disclosure with unnecessary details. The place information (place 1012) may be captured based on a connection with a tower, a server, a satellite, and/or a global positioning system (GPS), as is known in the art. Accordingly, detailed description is omitted so as not to obscure the present disclosure with unnecessary details. The sensory data 1014 includes observation data 1014S and/or communication data 1014C from the surroundings of the user. The observation data 1014S includes audio and visual environment around the user, for example, such as observations and episodic stories of a user through a classroom session as shown in FIG. 2B, a science laboratory in FIG. 2C, a round on golf course in FIGS. 2E, 2F, an inspection record and report in FIG. 2G. The communication data 1014C may include story of direct communication with the user, for example, lecture as shown in FIG. 2B, discussions as shown in FIG. 2C, and FIG. 2D. The communication data 1014C may include stories of indirect communication of the user, for example, communication through cognitive phone, as shown in FIGS. 3A and 3B. The sensory data 1014 also includes multimedia data downloaded from the Internet.

Additionally, in operation 1402, the cognitive capture apparatus 1100 also captures internal data of a user output from the user's body and brain 1000BB as user's response data 1000S and also generated from the user as user's emotional or cognitive state 1000E. The user may wear capture apparatus 1100 on user's head to capture cognitive data as shown in FIGS. 2A, 2B, 2C, 2D, 2F, 2G, and/or on other parts on the user's body to capture data. The user may also speak into a microphone of the capture apparatus, use a gesture and/or other actions to deliver user's internal cognitive data into the capture apparatus 1100.

In operation 1404, the cognitive processing system 1200 generates at least one timeline from data in the personal cognitive database 1240 in FIG. 1. The timeline is generated based on time information 1011 captured in operation 1402. The timeline includes a plurality of consecutive real-time-points . . . t−1, t, t+1, t+2 . . . of lifetime of the user. The size of the timeline is based on a duration of an episode of the sensory data captured in operation 1402.

In operation 1406, the cognitive processing system 1200 also generates and stamps consecutive episodic reference timepoints on the generated timeline of the user. That is, the generated timeline is divided into equal portions separated by reference timepoints. The timespan between two consecutive reference timepoints is the same.

In operation 1408, the user data is divided into consecutive data blocks (sensory data blocks 1231) of the same predetermined size. The user data includes one or more of communication data 1014C, observation data 1014S (including data downloaded from the Internet), user's emotional data 1000E, user's response data 1000S, a time component 1011, and a place component 1012. The time and place components 1011 and 1012 may be obtained from the environment 1010 and/or the user 1000 and/or external source(s). The user data is divided, by a computer or a server such as the cognitive producer 1230 of the cognitive processing system 1200, into a plurality of consecutive data blocks 1231(1), 1231(2) . . . 1231 (*n*) . . . (shown in FIG. 1), referred to as sensory data blocks.

The user data is divided based on the generated consecutive reference timepoints on the generated timeline. The length of a sensory data block is identical and equal to the timespan between two consecutive reference timepoints on the generated timeline of the user which is also determined based on the necessary time that a person uses to speak an average-length meaning with an average speed, according to an exemplary embodiment. The length may be from 2 seconds to 3 seconds. The length may be 2.16 seconds which may be the exact basic individual natural cycle of human's cognitive processes. The length may be 2 seconds which may be the nearest whole number to the basic individual natural cycle of human's cognitive processes.

In an exemplary embodiment, the internal and external data forms respective data blocks 1231 (sensory data blocks) based on respective time stamps. Data blocks include data that a user has been living with through his/her real-time, for example. It may include consecutive two-second episodes that have occurred in his/her lifetime. Each data block includes a two-second video of what the user was observing during these two seconds and the synchronized user's emotional data. In an exemplary embodiment, the user data is divided into the data blocks based on the reference timepoints stamped onto the timeline in operation 1406. That is, one reference timepoint is provided for each data block.

In operation 1410, an episodic data block is generated for each sensory data block. An episodic data block may include contextual components such as time component, place component, and an image component, according to an exemplary embodiment. In an exemplary embodiment, the episodic data block includes one or more cues 1232 (FIG. 1). Additionally, the episodic data block is stamped with the same reference timepoint as the respective sensory data block. That is, each episodic data block corresponds to a respective sensory data block and is stamped with the same reference timepoint.

According to an exemplary embodiment, an episodic data block may include an image cue. It may be a figure generated from a number of images within the respective sensory data block, as explained above. For example, if the length of sensory data block is two seconds, the number of images within that sensory data block may be 60 images. The system captures or obtains one image from the sixty images and then further simplifies this image to illustrate a cue which then represents the sixty other images. This solution minimizes the use of memory and speeds up the navigation during a recall process.

The time component of an episodic data block may be identified using the time captured by the user's device at the start of the respective sensory data block, the end of the respective sensory data block, the middle of the respective cognitive data block, or somewhere between the start and the end of the identified sensory data block, or any combination of these times, according to various exemplary embodiments. The time component of an episodic data block is the first or primary information to allocate a data block in a personal cognitive database 1240 (FIG. 1). In an exemplary embodiment described below, the middle time of a sensory data block is used as a primary component of an episodic block of the sensory data block. An episodic data block corresponding to a sensory data block is defined as the context that the user was existing in during the two-second episode within user's lifetime. An episodic block includes a time component such as 08:32:21 am on Apr. 16, 2019, a place component such as FUVI's headquarter, and an image component such as one of the images of what the user was viewing at this point of time (08:32:21).

In operation 1412, the cognitive processing system 1200 further analyzes visual information and audio information in each sensory data block to generate semantic cues. Semantic cues may be texts, symbols, and/or color codes that are obtained based on semantic analysis. The semantic cues represent the key content of the respective sensory data block. According to an exemplary embodiment, the semantic cues are in the linguistic forms which are most compatible with a human's mind and human's natural ability to recall information. A semantic cue is the first or primary information to stimulate a user to invoke information from an episodic memory. Semantic cues of an episodic sensory data block is defined as the key content that the user was observing or interacting with during the said two-second episode within user's lifetime. A semantic cue may be a noun, a verb, an adjective, a phrase or a sentence which helps a user recall an entire context and content of the two-second sensory data block. For example, the entire context and content of a cognitive data block is: at 2:00:01 pm on Mar. 6, 2007, the user was listening to a professor educating about learning and memory. The professor was saying that hippocampus is a key organ for learning and memory. Semantic cue that may be generated may include one or more of: hippocampus, key organ, learning and memory, hippocampus is a key organ for learning and memory. Additionally, a user may provide the semantic cues (inputting the semantic cue) including providing a keyword hippo, door of insight, HM, temporal lobe, or emotional cues based on the user's cognitive state.

Continuing with the operation 1412, the cognitive processing system 1200 also analyzes the user's data received directly from the user (user's response data 1000S and users cognitive state 1000E) during user's reviewing processes to generate user's own semantic cues to represent the key content of the respective sensory data block. The semantic cue may include a cognitive state of the user such as strong comprehension of the material or confused or bored with the material. The semantic data blocks respectively correspond to sensory data blocks by having a respective reference timepoint being stamped onto the block.

Next, enriched data may also be generated (not shown in FIG. 4). Enriched data contains different additional content that the user and users add into the respective data blocks. The enriched contents are from other sources and are not from the respective sensory data block. The enriched content may be videos, photos, comments, text captured by friends. It may be one or more files downloaded from the Internet. The enriched data is linked to a respective sensory data block or a respective semantic data block based on a reference timepoint.

In an exemplary embodiment, the generated data blocks are stored in a personal cognitive database 1240 (FIG. 1) and in operation 1414, the generated data is output on a timeline for a display. That is, the personalized timeline may be displayed to a user to assist in learning the material (sensory data captured by the capture apparatus 1100). In an exemplary embodiment, the personalized timeline may be displayed with corresponding episodic data blocks and/or corresponding semantic data blocks.

As explained above, the cognitive producer 1230 may link respective data blocks to form the personalized timeline which is stored in the personal cognitive database 1240. For example, the personal cognitive database 1240 includes sensory database 1241 which stores sensory data blocks, corresponding episodic database or episodic cued database 1242 which stores corresponding episodic data blocks, and a corresponding semantic database 1243 which stores corresponding semantic data blocks, and may also include corresponding enriched data (not shown).

As also explained above, the sensory database 1241 include sensory data 1014 that the user captures during his or her lifetime. For example, real-observation videos and photos along his or her lifetime including real-time viewing of videos, photos, and other contents on the user's computer e.g., downloaded from the Internet. According to an exemplary, the sensory database 1241 are stored on a cloud-based memory and are downloaded to a computer or a mobile device where the time information will correspond to approximately the time downloading and/or time of viewing the downloaded contents.

The episodic database 1242 may include simplified images such as (Img1), (Img2) . . . (Img n) . . . which are generated by cognitive producer 1230. Episodic data blocks, stored in the episodic database 1242, are used for quick navigation as shown in FIG. 1 and explained in further detail below. The episodic data blocks or a part of the episodic data blocks (episodic database 1242) are stored on a user's computer or a user's mobile device for quick navigation.

The semantic cued database 1243 includes semantic blocks (scaffolding units 1233). The semantic data blocks include semantic cues about the content of its respective sensory data block and may include texts (from voice to text conversion), symbols, and/or keywords obtained from user input. Additionally, a semantic cue may be blank to represent that the sensory data block is meaningless or almost meaningless to the user.

The enriched data includes different data related to cues. The enriched data is data which is not real-time observed and captured by the user from the environment. It may be videos or photos captured by friends or a definition, an image, a video downloaded from the internet and linked to the semantic data block. These are provided by way of an example and not by way of a limitation.

Figure 5:
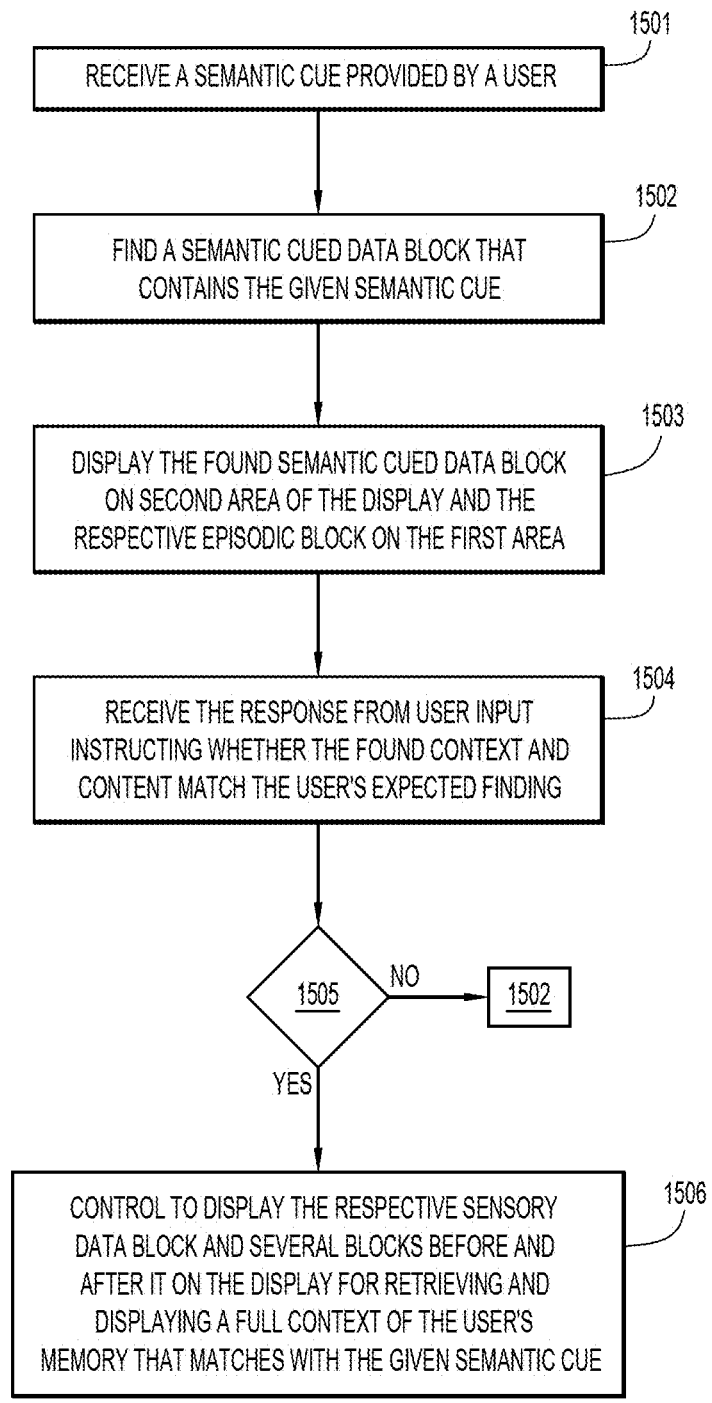
FIG. 5 is a flowchart illustrating a method of navigating the personal timeline, according to an exemplary embodiment.

FIG. 5 is a flowchart illustrating a method of navigating the personal timeline, according to an exemplary embodiment. In FIG. 5, information from the personal cognitive database 1240 is obtained based on a semantic cue provided or input by a user.

In operation 1501, the system receives a semantic cue provided by a user. According to an exemplary embodiment, the semantic cue may be obtained from a voice of the user received through a microphone of the system. According to another exemplary embodiment, the semantic cue may be a word or a phrase input by the user, via a user interface such as a keyboard. According to another example embodiment, a semantic cue may be selected via the user interface and may include an emotional state of the user/

In operation 1502, the processing system 1200 finds a semantic cued data block that contains the given semantic cue. That is, the processing system 1200 controls the navigator (the navigator 1245 in FIG. 1) to traverse the episodic data blocks to find a first semantic block that contains the input semantic cue.

In operation 1503, the processing system 1200 controls the display to display the found semantic cued data block that contains the given semantic cue on the second area of the display and its respective episodic block on the first area of the display.

In operation 1504, the processing system 1200 receives the response from the user (user input) instructing or indicating whether the found context and content match the user's expected finding.

In operation 1505, the processing system 1200 processes the user's instruction (user input) to determine whether the found context matches the user's expected finding. If the user's instruction is NO, the process goes back or returns to the operation 1502, and the processing system 1200 controls the navigator to continue going along the user's timeline to find another semantic block that contain the given semantic cue.

If the user's instruction is YES in operation 1505, the process goes to operation 1506.

In operation 1506, the processing system 1200 control to display the respective sensory data block and several blocks before and after it on the display. That is, the processing system 1200 controls the display to play a video (or display a plurality of consecutive images embodied in the found sensory data block or blocks) including the found sensory data block and/or several consecutive sensory data blocks before and after the found sensory data block for retrieving the full context of the user's episodic memory that matches with the given semantic cue.

Figure 6:
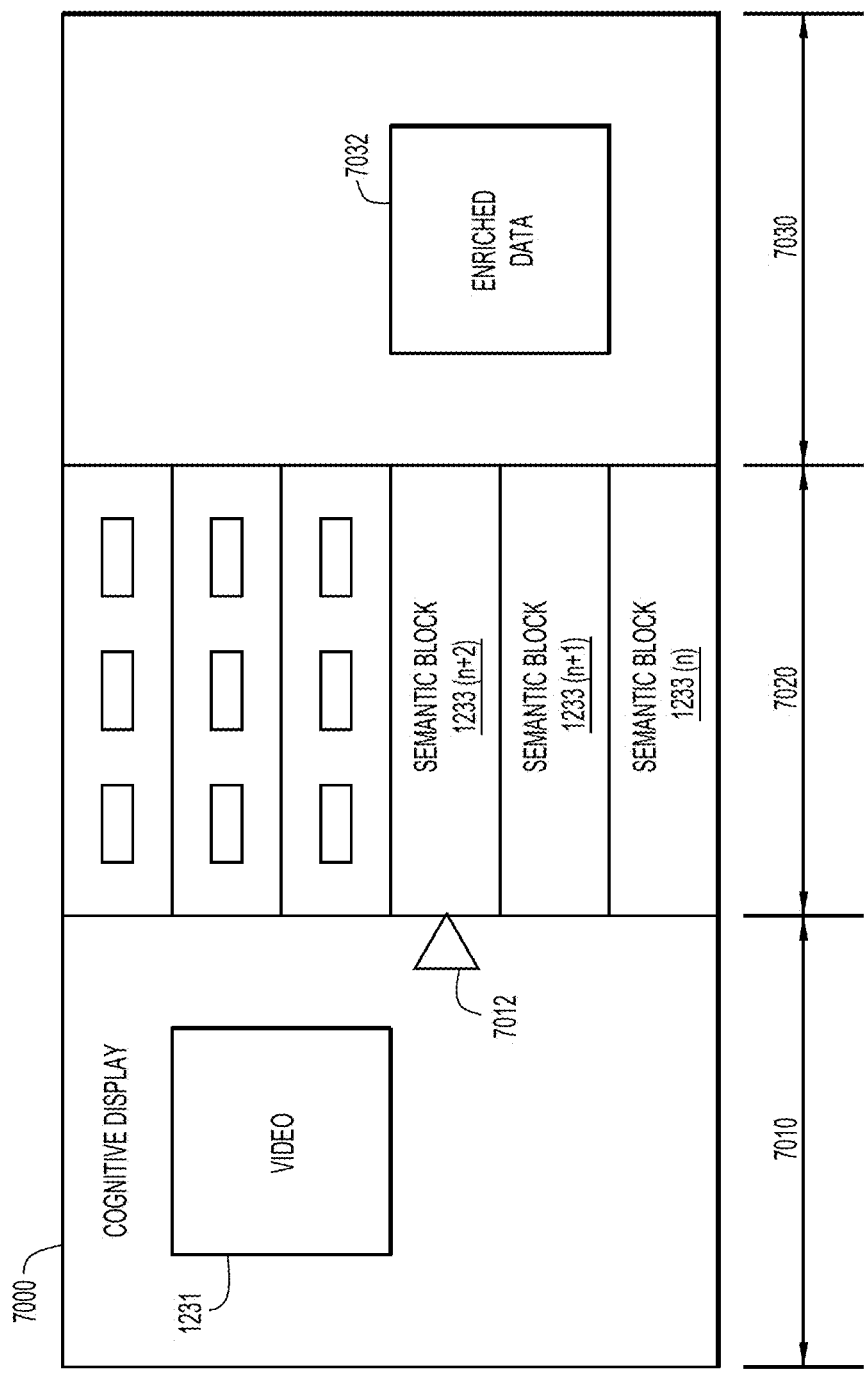
FIG. 6 is a view illustrating a cognitive display, according to an exemplary embodiment.

FIG. 6 is a view illustrating a cognitive display that is displayed on a display, according to an exemplary embodiment. As shown in FIG. 6, the cognitive display 7000 includes a first display area 7010 in which a plurality of sensory data blocks 1231 of FIG. 1 is displayed. For example, the system may play a video of a lecture in the first display area 7010. In FIG. 6, the cognitive display 7000 may further includes a second display area 7020 in which corresponding semantic data blocks (scaffold units 1233) are displayed. As shown in FIG. 6, the second display area 7020 displays a plurality of consecutive semantic data blocks (scaffold units 1233) (n, n+1, n+2). An indicator 7012 may be provided to indicate a semantic data block 1233 that is currently being played as video (corresponding sensory data block 1231). A third display area 7030 may include enriched data 7032 obtained from the data stored in an enriched database.

The cognitive display 7000 may further display a tool (not shown) on the first display area 7010. The tool allows the user to have at least two options: displaying two areas or three areas. In case of the selection for displaying two areas, the user can expand the sensory data and the corresponding semantic data blocks, as explained in further detail with reference to FIG. 7, which is a view illustrating a cognitive display, according to another example embodiment.

Figure 7:
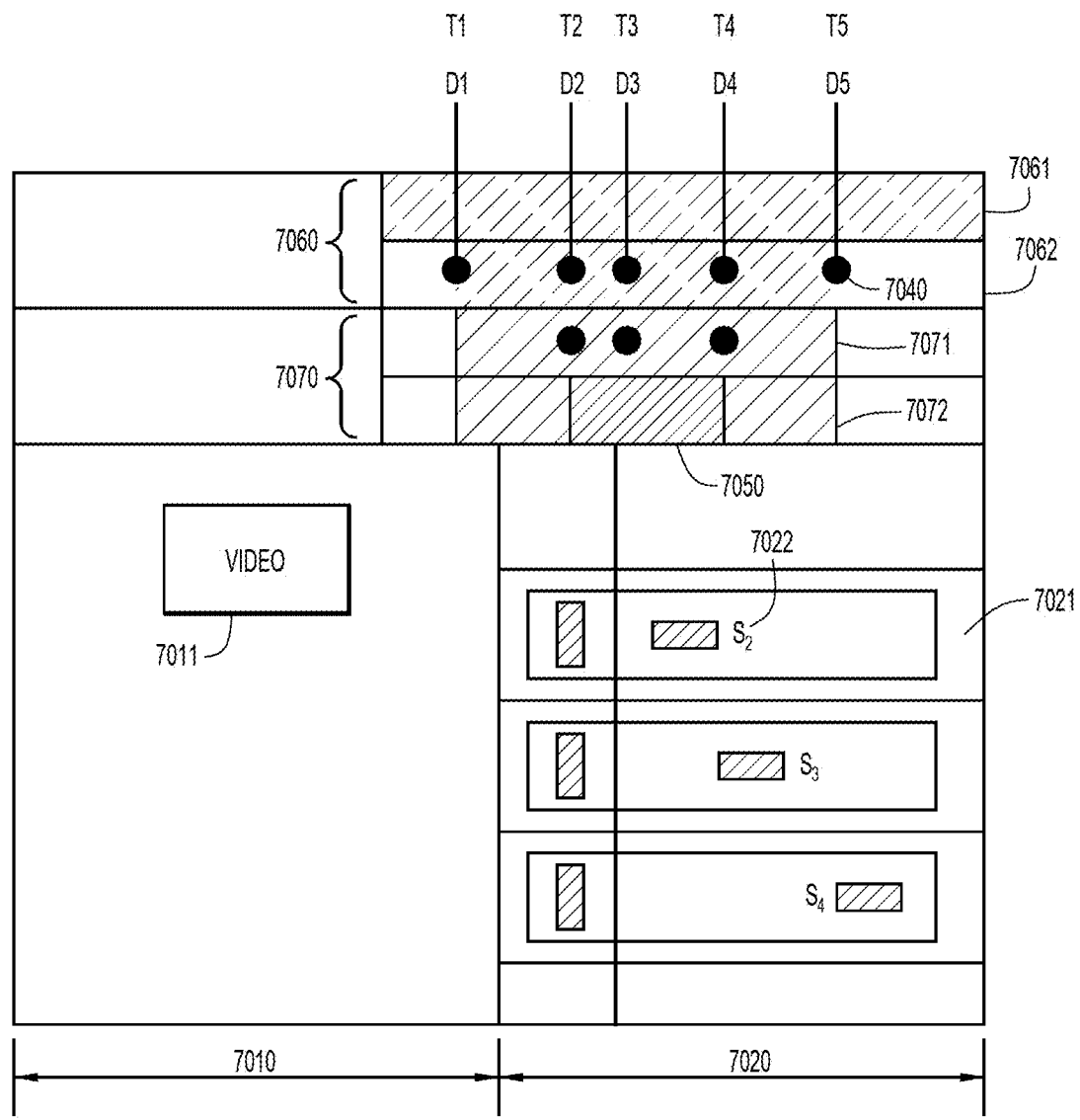
FIG. 7 is view illustrating a cognitive display, according to another exemplary embodiment.

In FIG. 7, the cognitive display has the first display area 7010 and the second display area 7020. The first display area 7010 displays the sensory data blocks in a form of a video 7011. The second display area 7020 displays corresponding semantic data blocks in a form of text blocks 7021. In an exemplary embodiment, the second display area 7020 displays text which is converted based on the audio of the video 7011. Additionally, the text blocks 7021 include semantic cues 7022 (such as keywords S2, S3, and S4). The semantic cues 7022 may be displayed in an emphasized manner, as shown in FIG. 7.

Additionally, in FIG. 7, timelines 7060 and 7070 are displayed. The first timeline 7060 corresponds to a short-term memory and the second timeline 7070 corresponds to a long term memory. In an example embodiment, flashing dots 7040 and color coded highlighted portions 7050 are displayed on the first timeline 7060 and/or the second timeline 7070 when the user is impressed and/or a predetermined level of comprehension is obtained during the cognitive processes of the user. In FIG. 7, D1, D2, D3, D4, D5 are the flashing dots at the timepoints T1, T2, T3, T4, and T5. In an exemplary embodiment depicted in FIG. 7, a flashing dot 7040 is a cue which indicates a position of a timepoint when the user was impressed (a pulse happening in a short period of time) and a color coded highlighted portion 7050 is a cue indicating an interesting, useful and liked episode of the video after the user viewed it (a period of time). A color coded highlighted portion usually includes several flashing dots, by way of an example and not by way of a limitation.

In FIG. 7, four different phases of receiving and transferring the data into cognitive insights of the user are shown. The first phase 7061 is the receiving (including observation, capturing and/or downloading) phase, the second phase 7062 is the skimming phase, the third phase 7071 is the working (including review, rehearsal, and linking effort) phase, and the fourth phase 7072 is consolidated and comprehensive phase. The data in an area represented by the first timeline 7060 include the first phase 7061 and the second phase 7062 and belong to the short-term memory. The data in an area represented by the second timeline 7070 include the third phase 7071 and the fourth phase 7072 and belong to the long-term memory.

Figure 8:
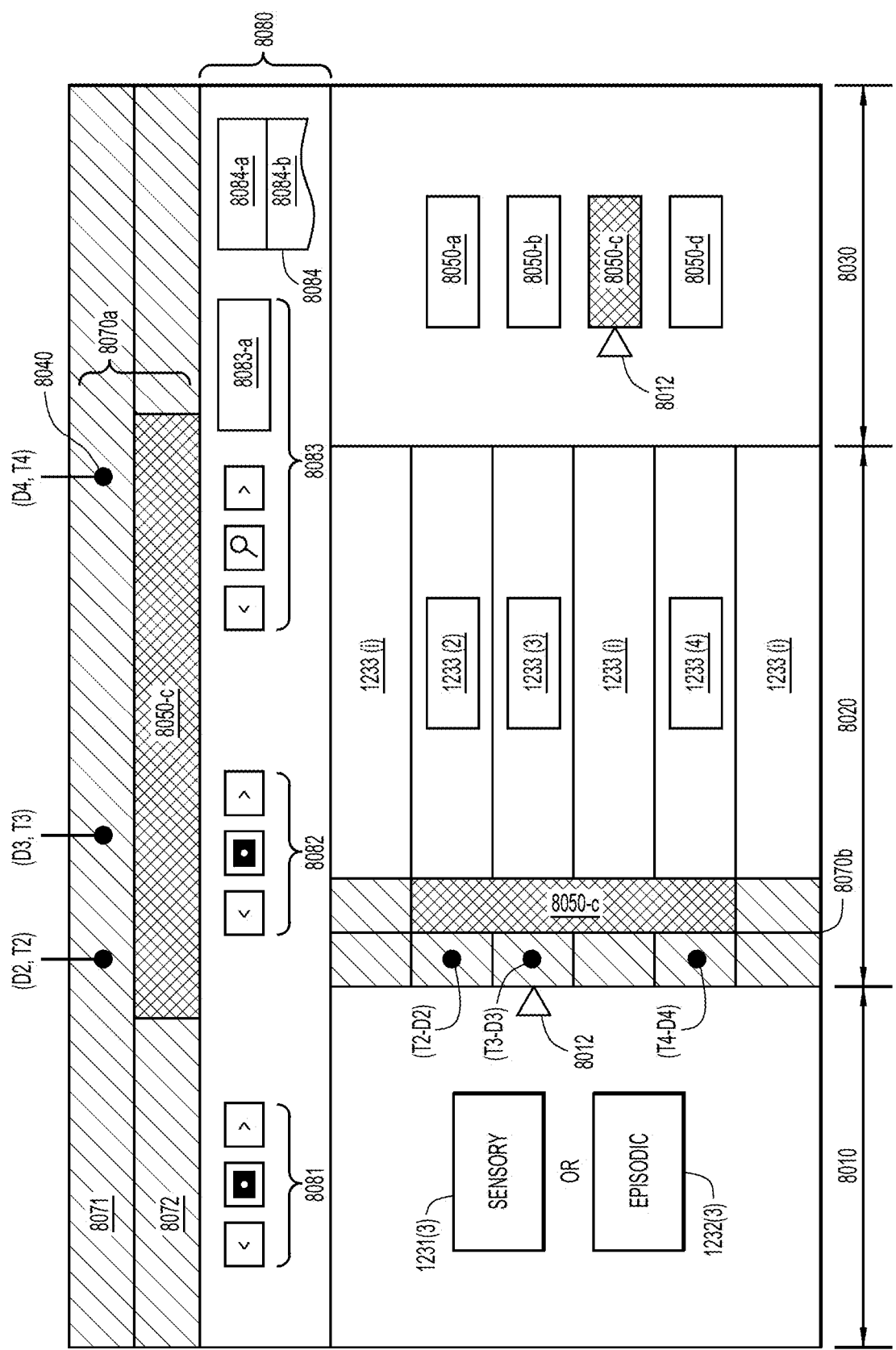
FIG. 8 is a view illustrating another cognitive display according to yet another exemplary embodiment.

FIG. 8 is a view illustrating another cognitive display, according to yet another exemplary embodiment.

In FIG. 8, the first area 8010 displays the sensory data blocks 1231 and/or the episodic data blocks (cues 1232). The second area 8020 displays corresponding semantic data blocks (scaffold units 1233) where the semantic data block (scaffold unit 1233(3)) corresponds to a current sensory block 1231(3) and/or the current episodic block (cue 1232(3)).

A video is played in the first area 8010. A plurality of consecutive semantic blocks (scaffold unit 1233($i$)) is displayed in the second area 8020 in which, the semantic blocks (scaffold units 1233(2), 1233(3), 1233($i$), and 1233(4)) are highlighted.

At the side of the second area 8020, a vertical timeline 8070$b$ is allocated to link the respective blocks with the reference timepoints on the timeline. Flashing dots 8040—D2, D3, and D4 are also linked with reference timepoints T2, T3, and T4. Color coded highlighted portion such as the portion that include a cue 8050$c$ indicates that the content from T2 to T4 is comprehended and useful for the user in the future. In an exemplary embodiment, the color coded highlighted portion (portion that includes the cue 8050-$c$ indicates that the content is comprehended by the user and has semantic meaning that is useful for the user e.g., the content helps user understand why 1233(4)=1233(2)+1233(3), user likes this content, user will review and use it for his/her presentation in future and so on.

In a third display 8030, enriched data which includes additional notes and external contents such as google searches, dictionary definitions, and so on, may be displayed (not shown).

As an exemplary embodiment, in the third display 8030 of FIG. 8, a list of semantic cues 8050-$a$, 8050-$b$, 8050-$c$, and 8050-$d$ which relate to the key contents of the respective color coded highlighted portions is displayed. An indicator 8012 is provided to indicate that the color coded highlighted video portion that includes the semantic cue 8050-*c* is currently being played. The other portions (semantic cues 8050-*a* and 8050-*b*) are the earlier portions and a portion (semantic cue 8050-*d*) is the later portion.

Similar to the second timeline 7070 in FIG. 7, in FIG. 8, there is a timeline 8070*a* which is divided into two areas: a first area 8071 and a second area 8072. In an exemplary embodiment depicted in FIG. 8, the timeline 8070*a* corresponds to a long-term memory. Similar to the second timeline 7070 in FIG. 7, the timeline 8070*a* has two areas, the first area 8071 dedicated to the third phase and the second area 8072 dedicated to the fourth phase.

The first area 8071 of the timeline 8070*a* includes the third phase obtained during the viewing and/or working of the contents i.e., during the review of the captured sensory data blocks 1231 and/or episodic data blocks (cues 1232). In the first area 8071, the positions of cued data blocks are shown by flashing dots 8040 D2, D3, and D4 at the respective reference timepoint T2, T3, and T4.

The second area 8072 of the timeline 8070*a* includes the fourth phases, when contents is committed to long term memory. In the second area 8072, the contents is displayed as a color coded highlighted portion (portion that includes the semantic cue 8050-*c*) to indicate that it has been comprehended by the user and is useful to the user in the future. User may introduce this content to other users.

In FIG. 8, there is also a control area 8080, which includes different input interfaces for user to control the processes and to control the cognitive display shown in FIG. 8.

For example, a first user interface 8081 provides for user manipulations of jumping between various flashing dots 8040 in the first area 8071 of the timeline 8070*a*. That is, the user manipulates the first user interface 8081 to jump forward and backward to a next flashing dot.

A second user interface 8082 provides for user manipulations of jumping between various highlighted portions in the second area 8072 of the timeline 8070*a*. That is, the user manipulates the second user interface 8082 to jump forward and backward to a next color coded highlighted portion.

A third user interface 8083 provides for user manipulations of jumping to a key word, jumping forward and backward to a next position of that key word. That is, the user type a key word into box 8083-*a* of the third user interface 8083 and manipulates icon > or < to jump forward and backward to the next positions of the key word in the video (which is inputted in the box 8083-*a*).

A fourth user interface 8084 displays a list of cued semantics (created by viewer) or suggested semantics (generated by the user). The user manipulates the fourth user interface 8084 to jump directly to the expected content. The fourth user interface 8084 depicts a first semantic cue 8084-*a* and a second semantic cue 8084-*b*.

FIGS. 9A-10B are views illustrating different methods of generating semantic cues and obtaining comprehension of the contents, according to various exemplary embodiments.

Figure 9A:
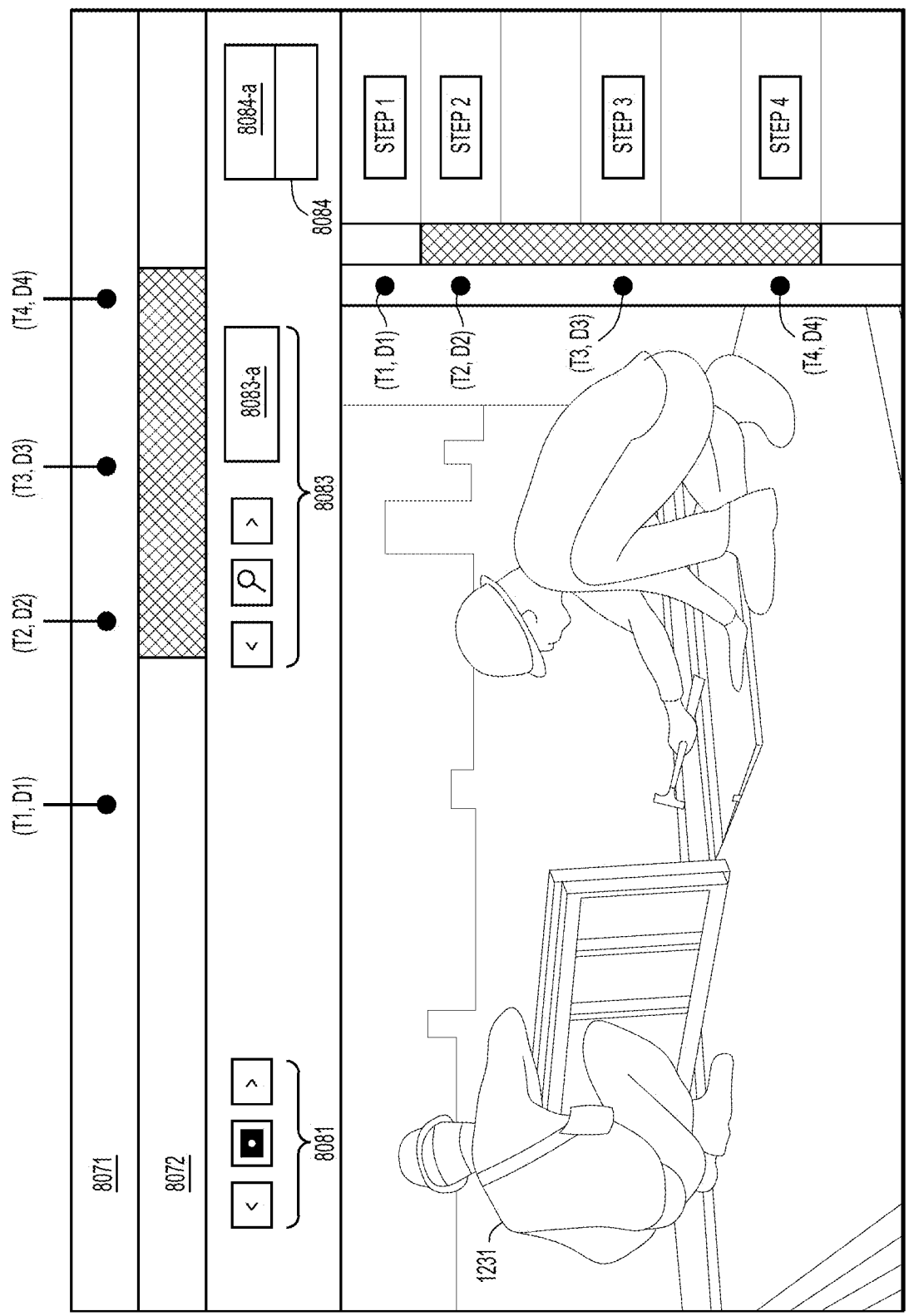
FIGS. 9A-9D are views illustrating a process of learning contents by progressing through different phases of the cognitive learning processes in which the sensory data is committed to a long-term memory, according to various exemplary embodiments.

As shown in FIG. 9A, the sensory data blocks 1231 (a video) illustrate a process of installing slab formwork. In an exemplary embodiment of FIG. 9A, the first area of a display only includes a video portion and not an audio portion of the contents. For example, there may be no corresponding audio portion. As such, the semantic cues depicted in the second area of a display may include symbols and/or text such as "step 1", "step 2", "step 3", and "step 4" may be input by a user via a user interface such as a keyboard and/or a touch screen. In another exemplary embodiment, image processing may be performed to obtain corresponding semantic cues, displayed on a right of the display depicted in FIG. 9A.

Additionally, in an exemplary embodiment depicted in FIG. 9A, flashing dots and color coded highlighted portions are generated based on the analyzing of the emotional data of the user (the cognitive state of the user) and/or based on the user input received via the user interface.

In FIG. 9A, the user is navigating the semantic cues to find and view the step 3 of the installation process. The user may find the step of the installation process that describes how to use a pin to connect two panels, by way of one or more of the following techniques.

1) The user may remember that "step 3" contains the expected content. He/she may decide to input a keyword "step 3" into an input box 8083*a* of the third user interface 8083. Based on the input keyword, the system navigates directly to the expected semantic block that contains the input keyword "step 3".

2) The user may click the first user interface 8081 to navigate to the expected step via the flashing point in the first area 8071 of the timeline.

3) The user may simply input "step" into the input box 8083*a* and manipulate the third user interface 8083 to go forward to see from step 1, step 2 until the right one is step 3 (which he/she sees "how to use the pin" in the video displayed on the first area of the display). That is, by manipulating the third user interface 8083, the user may consecutively jump through step 1, step 2, . . . , until finding or navigating to the expected point of step 3.

4) The user may select the semantic cue from a list of semantic cues (displayed on a fourth user interface 8084). For example, the user may select "step 3", a semantic cue 8084-*a* from the list of semantic cues displayed in the fourth user interface 8084 (the list includes step 1, step 2, step 3, step 4 . . . step 10).

Figure 9B:
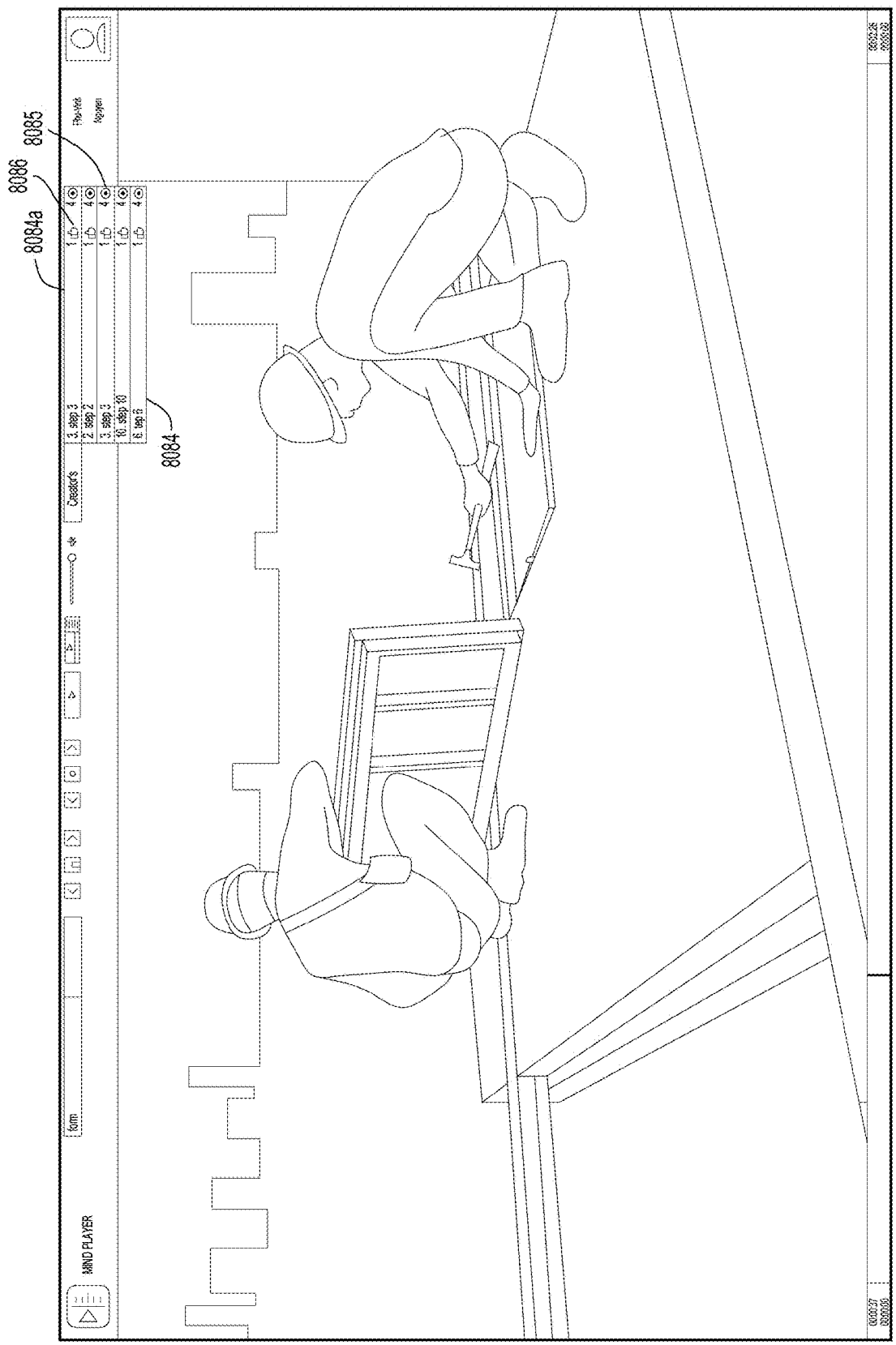
Figure 9C:
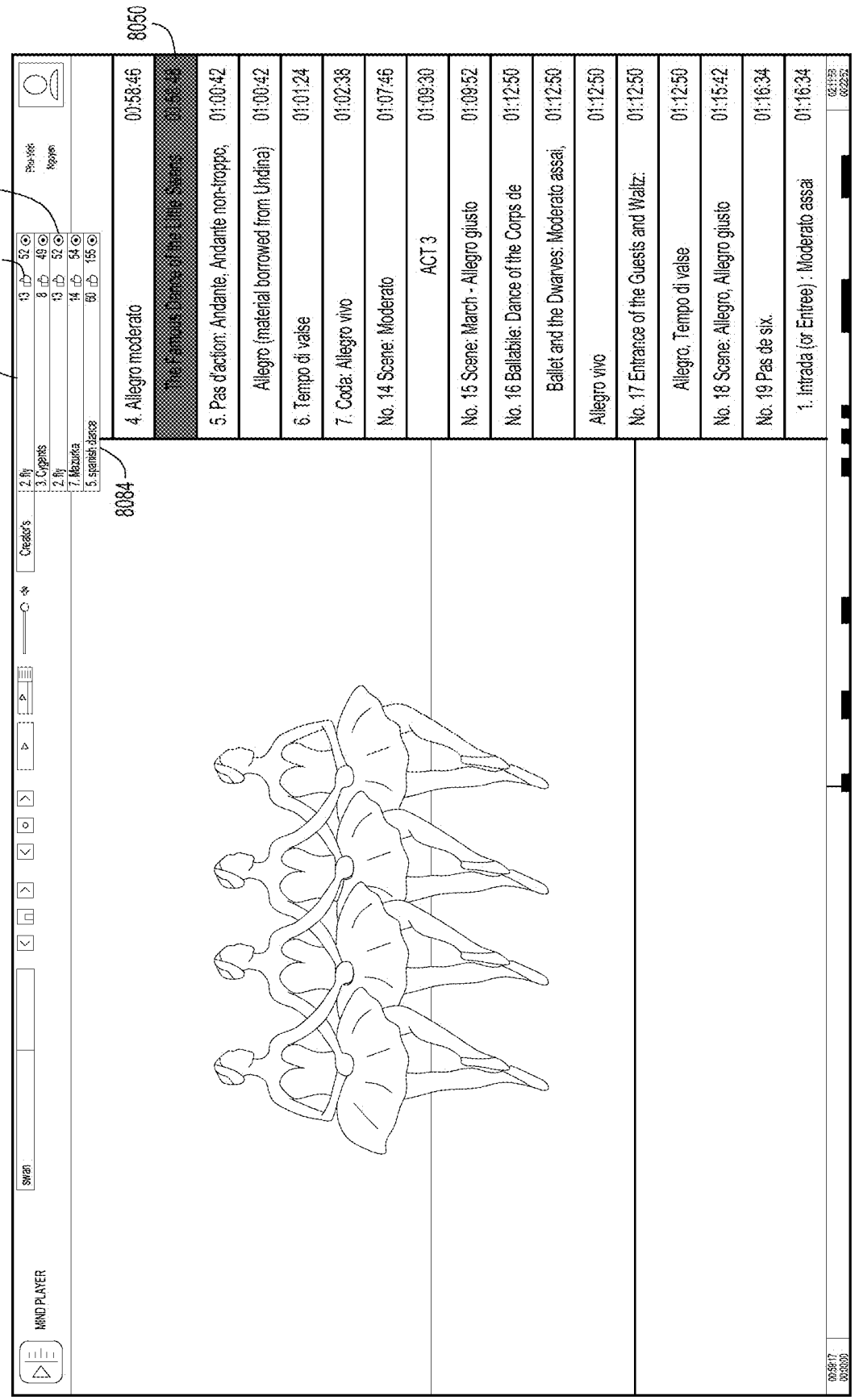
Figure 9D:
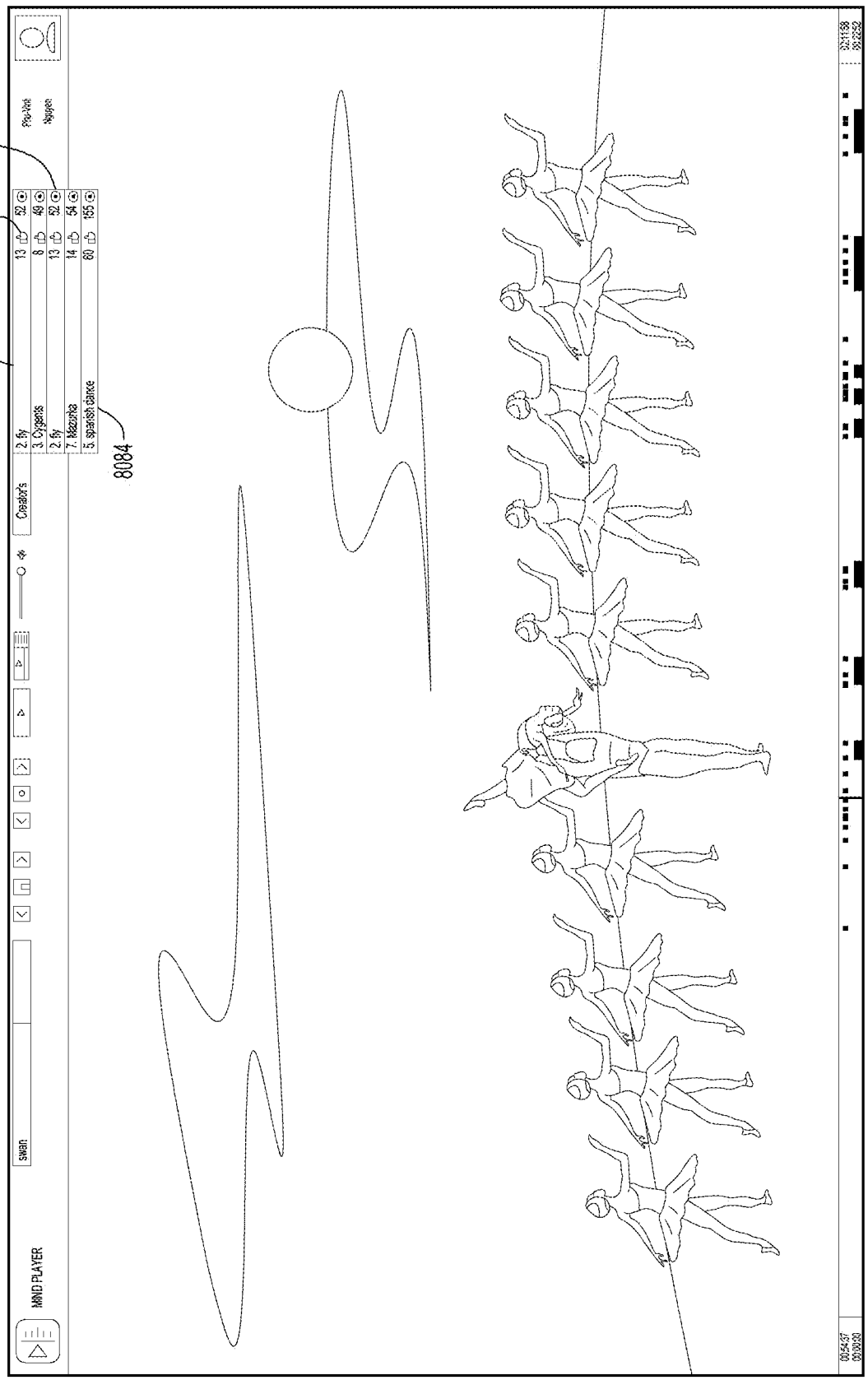

FIGS. 9B, 9C, and 9D are views illustrating the fourth user interface 8084, according to various exemplary embodiments. In FIG. 9B, the fourth user interface 8084 displays a list or a drop down menu of semantic cues and a box displays the selected semantic cue 8084-*a* from the list ("step 3"). In FIG. 9C, the user may use the fourth user interface 8084 to jump to "Cygnets" or "Dance of the little swans" semantic block.

In FIG. 9C, a table of key contents 8050 may be displayed on the right side of a display. That is, the content may be navigated based on semantic cues displayed in a form of a table of key contents 8050 in the second area of the display. In FIG. 9C, the user may use the fourth user interface 8084 to jump to a "flying" semantic block, which is shown in FIG. 9D. That is, by navigating the fourth user interface 8084, the user jumps to contents that have a semantic cue "fly", as shown in FIG. 9D. According to various exemplary embodiments, the semantic list shown in the fourth user interface 8084 may be generated by a user. The user may provide custom labels to various portions of the contents, thereby generating individualized semantic cues. In exemplary embodiments depicted in FIGS. 9B-9D, the semantic cues may also include a number of people who viewed the contents (shown with a view indicator 8085) and a number of people who liked the contents (shown with a like indicator 8086).

Figure 10A:
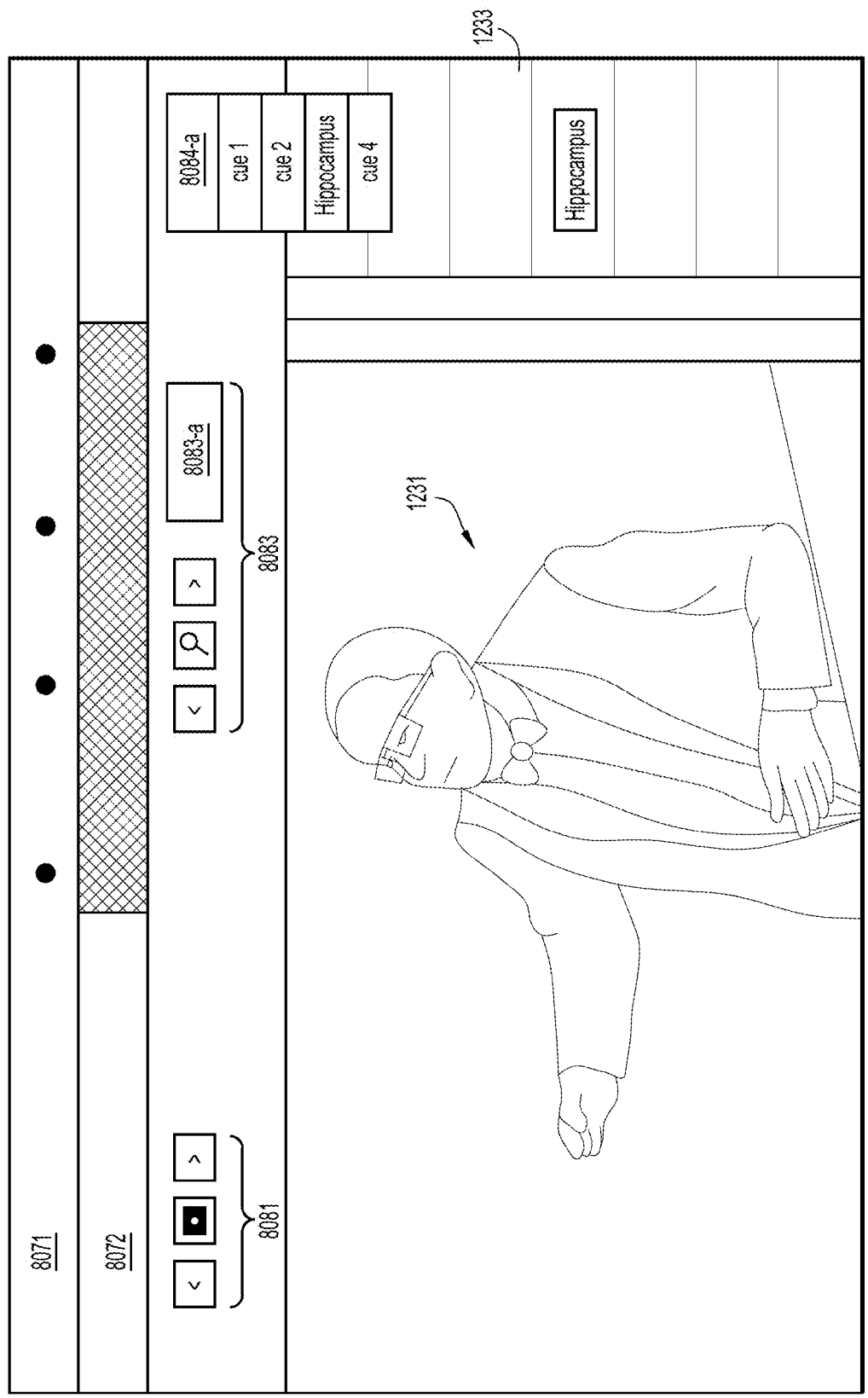
FIGS. 10A and 10B are views illustrating a navigation of a cognitive display, according to various exemplary embodiments.
Figure 10B:
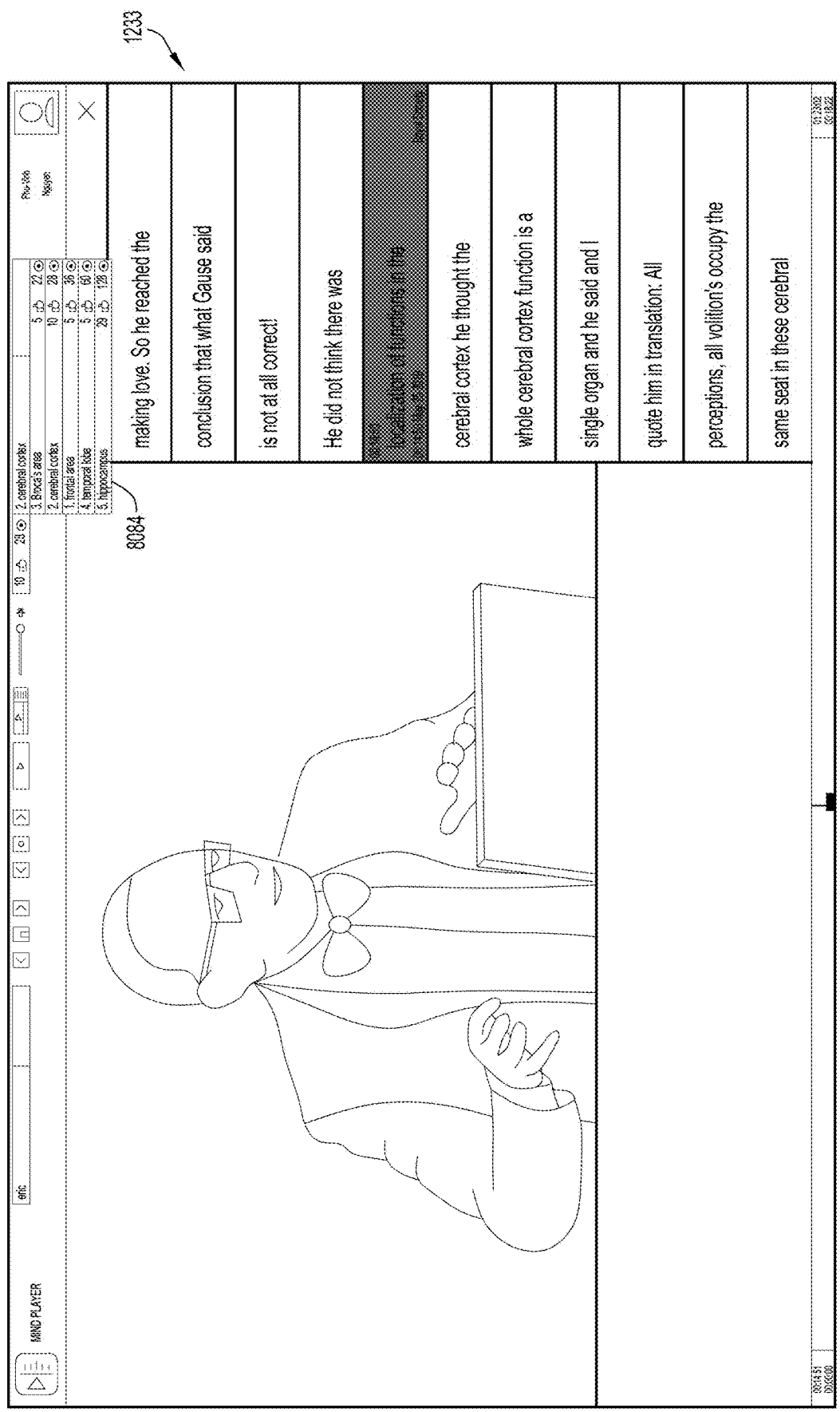

In FIGS. 10A and 10B are views illustrating navigating semantic cues and forming cognitive insights, according to another exemplary embodiment. In FIG. 10A, the sensory data blocks 1231 illustrate a video lecture which include audio data in a form of a voice of a professor. The semantic data blocks (scaffold units 1233) are generated through a voice-to text conversion and depicted on the right of the display (FIG. 10B). The semantic cues in a form of symbols and/or text such as "hippocampus" can be selected, by a user, from the texts in the semantic data blocks. Flashing dots and color coded highlighted portions may be generated by analyzing emotional data of the user (cognitive state of the user). They are also created through an interface such as a keyboard and/or a touch screen.

In order to find what the professor is saying about the semantic cue "hippocampus", the user can navigate the data in the following exemplary methods.

1) The user may click on the first user interface 8081 to navigate to "hippocampus" through flashing points depicted in the first area 8071 of the timeline.

2) The user may type in the keyword "hippocampus" into an input filed 8083a to go directly to the expected point if user is sure the expected content is "hippocampus".

3) The user may use a pull down list of the fourth user interface 8084 to select "hippocampus" in the list of listed semantic cues cue 1, cue 2, hippocampus, cue 4.

FIG. 10B is a view illustrating that the user is using the fourth user interface 8084 to jump to the semantic "cerebral cortex" which also appear on the second area of the display, according to an exemplary embodiment. The list of semantic cues are shown in the fourth user interface 8084 in FIG. 10B (in a form of a pull down menu). These cues may be generated by a user.

Figure 11:
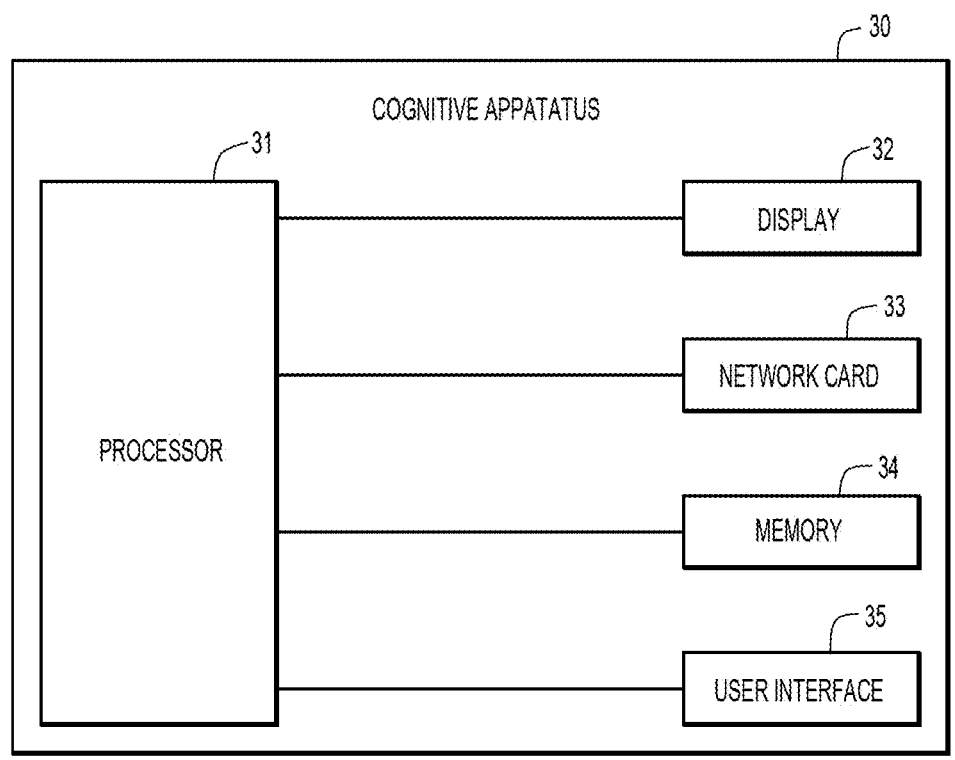
FIG. 11 is a block diagram illustrating hardware components of a cognitive apparatus, according to an exemplary embodiment.

FIG. 11 is a block diagram illustrating hardware components of a cognitive apparatus, according to an exemplary embodiment.

In FIG. 11, a cognitive apparatus (an apparatus 30) may be a server and/or include one or more computers. The apparatus 30 is a processing apparatus, which includes a processor 31, which may be a central processing unit (CPU), which controls the apparatus and its hardware components and executes software instructions stored in one or more memories such as a memory 34. By way of an example, the processor 31 may also include a random access memory (RAM), a read only memory (ROM), one or more graphical processes, interfaces, and so on. Components of the processor 31 may be connected to each other via a bus. The processor 31 is further connected to and controls a display 32, which outputs recorded or original video signals in various forms and formats. The display 32 includes a speaker which outputs an audio sound. This is provided by way of an example and not by way of a limitation. Multiple speakers may be provided and maybe external to the display 32. The processor 31 may be connected to a network interface or a network card 33, which may include a WiFi chip, a Bluetooth chip, wireless network chip, and so on. The network card 33 may further include one or more ports for wired connections. Additionally, the apparatus 30 may include a memory 34, which may store one or more of executable instructions which when executed by the processor 31 cause the processor to control the apparatus 30 and its components. The memory 34 may further store audio and video data (contents) generated by one of the capture apparatus (see e.g. FIGS. 1-3B). The apparatus 30 may further include a user interface 35, which may include buttons, keyboard, a mouse, a USB port, a microphone, a gesture sensor, and so on. The user interface 35 receives user input in various formats such as gestures, audio via a microphone, keyboard, mouse, touch screen, and so on, provided by way of an example and not by way of a limitation.

In an exemplary embodiment, the processor 31 executes the cognitive processing system 1200 shown in FIG. 1.

Many changes may be apparent to those of ordinary skill in the art without departing from the scope and spirit of the described embodiments. The terminology used herein was chosen to best explain the principles of the embodiments, the practical application or technical improvement over technologies found in the market place or to enable ordinary skill in the art to understand the embodiments disclosed herein.

In an exemplary embodiment, the term "computer-readable medium" as used herein refers to any medium that participates in providing instructions to a processor for execution. A computer readable medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable medium would include the following: an electrical connection having two or more wires, a portable computer diskette such as a floppy disk or a flexible disk, magnetic tape or any other magnetic medium, a hard disk, a random access memory (RAM), a read-only memory (ROM), an erasable programmable read-only memory (EPROM or Flash memory), a memory card, any other memory chip or cartridge, an optical fiber, a portable compact disc read-only memory (CD-ROM), any other optical medium, punchcards, papertape, any other physical medium with patterns of holes, or any other medium from which a computer can read or suitable combination of the foregoing.

In the context of this document, a computer readable medium may be any tangible, non-transitory medium that can contain, or store a program for use by or in connection with an instruction execution system, apparatus, or device.

Another form is signal medium and may include a propagated data signal with computer readable program code embodied therein, for example, in a base band or as part of a carrier wave. Such a propagated signal may take any of a variety of forms, including, but not limited to, the electromagnetic, optical, or any suitable combination thereof. The signal medium may include coaxial cables, copper wire and fiber optics, including the wires that comprise data bus. The signal medium may be any medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire line, optical fiber cable, RF, etc. or any suitable combination of the foregoing.

Computer program code for carrying out operations for aspects of the exemplary embodiments may be written in any combination of one or more programming languages, including an object oriented programming language such as Java, Smalltalk, C++, .Net or the like and conventional procedural programming languages. The program code may execute entirely on the user's computer, partly on the user's computer, as a stand-alone software package, partly on the user's computer and partly on a remote computer or entirely on the remote computer or server. The remote computer may be connected to the user's computer through any type of network, including a local area network (LAN) or a wide area network (WAN), or the connection may be made to an external computer (for example, through the Internet using an Internet Service Provider).

The computer-readable medium is just one example of a machine-readable medium, which may carry instructions for implementing any of the methods and/or techniques described herein. Such a medium may take many forms, including but not limited to, non-volatile media and volatile media. Non-volatile media includes, for example, optical or magnetic disks. Volatile media includes dynamic memory.

Various forms of computer readable media may be involved in carrying one or more sequences of one or more instructions to a processor such as a CPU for execution. For example, the instructions may initially be carried on a magnetic disk from a remote computer. Alternatively, a remote computer can load the instructions into its dynamic memory and send the instructions over a telephone line using a modem. A modem local to a computer system can receive the data on the telephone line and use an infra-red transmitter to convert the data to an infra-red signal. An infra-red detector can receive the data carried in the infra-red signal and appropriate circuitry can place the data on the data bus. The bus carries the data to the volatile storage, from which processor retrieves and executes the instructions. The instructions received by the volatile memory may optionally be stored on persistent storage device either before or after execution by a processor. The instructions may also be downloaded into the computer platform via Internet using a variety of network data communication protocols well known in the art.

The flowchart and block diagrams in the Figures illustrate the architecture, functionality, and operation of possible implementations of systems, methods and computer program products according to various exemplary embodiments. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or two blocks may sometimes be executed in the reverse order, depending upon the functionality involved. It will also be noted that each block of the block diagram and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology as used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or acts for performing the function in combination with other claimed elements as specifically claimed.

The description of the exemplary embodiments has been presented for purposes of illustration and description, but is not intended to be exhaustive or limiting in any form. Many modifications and variations will be apparent to those of ordinary skill in the art without departing from the scope and spirit of the invention. Exemplary embodiments were chosen and described in order to explain operations and the practical applications thereof, and to enable others of ordinary skill in the art to understand various embodiments with various modifications as are suited to the particular use contemplated. That is, various modifications to these embodiments will be readily apparent to those skilled in the art, and the generic principles and specific examples defined herein may be applied to other embodiments without the use of inventive faculty. For example, some or all of the features of the different embodiments discussed above may be combined into a single embodiment. Conversely, some of the features of a single embodiment discussed above may be deleted from the embodiment. Therefore, the present disclosure is not intended to be limited to exemplary embodiments described herein but is to be accorded the widest scope as defined by the features of the claims and equivalents thereof.

What is claimed is:

1. A method of providing individualized cognitive assistance, the method comprising:
   receiving, by a computer, data comprising visual and audio information observed by a user, a corresponding time information, and a corresponding location information;
   generating, by the computer, at least one timeline related to a time period in which the data was obtained by the user;
   generating and stamping, on the at least one timeline, a plurality of consecutive episodic reference timepoints, which are spaced apart equidistant from one another;
   dividing the data into a plurality of consecutive sensory data blocks, the plurality of consecutive sensory data blocks have the same predetermined size and each of the plurality of consecutive sensory data blocks comprises one reference timepoint from among the plurality of consecutive episodic reference timepoints;
   generating a semantic data block for each of the plurality of consecutive sensory data blocks, wherein each of the semantic data block comprises at least one semantic cue related to a meaning of content of the respective sensory data block, and stamping the reference timepoint of the respective sensory data block onto the respective semantic data block;
   displaying, in a first area of a display, the plurality of consecutive sensory data blocks and in a second area of the display, a corresponding plurality of semantic data blocks that are synchronized with the plurality of consecutive sensory data block based on the stamped reference timepoint;
   receiving, via a user interface of the computer, an input from the user comprising at least one semantic cue;
   searching a plurality of consecutive semantic data blocks to find one semantic data block comprising the semantic cue that is input by the user via the user interface;
   displaying, in the second area of the display, a first found semantic data block based on the searching and displaying the respective sensory data block in synchronization with the first found semantic data block;
   receiving an additional input from the user comprising one of a confirmation of the first found semantic data block or a rejection of the first found semantic data block; and
   based on the additional input comprising the rejection of the first found semantic data block, continue searching in succeeding plurality of semantic data blocks to find a next found semantic data block comprising the semantic cue that is input by the user and displaying the next found semantic data block in the second area of the display and the respective sensory data block in synchronization with the next found semantic data block.

2. The method according to claim 1, further comprising:
generating an episodic data block for each of the plurality of consecutive sensory data blocks, the episodic data block comprises at least one episodic cue generated by simplifying a plurality of images of the visual information of the respective sensory data block from among the plurality of consecutive sensory data blocks, and stamping the reference timepoint of the respective sensory data block onto the respective episodic data block; and
displaying a plurality of consecutive episodic data blocks in the first area of the display synchronized with the corresponding plurality semantic data blocks in the second area of the display, based on the stamped reference timepoint,
wherein the at least one semantic cue of the semantic data block is at least one of a blank, a text, a symbol, a flashing dot, and a color-coded highlight.

3. The method according to claim 2, further comprising:
generating the at least one semantic cue of said each semantic data block which is the at least one of the blank, the text, the symbol, the flashing dot, and the color highlight, based on at least one semantic analysis of the respective sensory data block and based on the user input.

4. The method according to claim 3, further comprising:
receiving another input from the user comprising a first selection of a position of a navigation start indicating a starting reference timepoint on the at least one timeline and a second selection of a forward navigation or a backward navigation; and
consecutively displaying a plurality of consecutive positions of consecutive reference timepoints starting from the starting reference timepoint on the second area of the display, and the respective plurality of the consecutive semantic blocks in the second area of the display in synchronization with the respective plurality of consecutive episodic block in the first area of the display.

5. The method according to claim 1, further comprising:
based on the additional input comprising the confirmation of the one semantic data block, consecutively displaying a plurality of consecutive semantic data blocks starting from at least one first semantic data block preceding the first found semantic data block and until receiving another input to end the displaying and consecutively displaying, in the first area of the display, a respective plurality of consecutive sensory data blocks in synchronization with the plurality of the displayed consecutive semantic data blocks.

6. The method according to claim 1, further comprising:
displaying on a third area of the display the at least one timeline which comprises a first timeline and a second timeline,
wherein the first timeline comprises the plurality of consecutive reference timepoints which are linked with the plurality of the respective sensory data blocks, and
wherein the second timeline comprises a set of consecutive reference timepoints from among the plurality of consecutive reference timepoints that are linked to a set of sensory data blocks from among the plurality of the consecutive sensory data blocks, wherein the set of sensory data blocks have been viewed at least once before by the user.

7. The method according to claim 1, wherein the data comprises sensory data captured from the user by an apparatus, the visual and audio information is environment observed by the user, and the sensory data is a cognitive state of the user with respect to the environment.

8. The method according to claim 1, wherein the visual and audio information is at least one of:
the audio information is at least one of first communication data communicated by the user during an established communication with another entity via a network or a second communication data communicated to the user by the another entity during the established communication, or
the visual information is contents downloaded from the network and observed by the user.

9. The method of according to claim 1, wherein the data observed by the user comprises at least one of:
first data including sensory data obtained from a first source and the visual and audio information comprises an environment observed by the user and the sensory data comprises cognitive state of the user with respect to the environment, or
second data obtained from a second source different from the first source, the second source including multimedia data being downloaded via a network and observed by the user.

10. The method of claim 1, further comprising:
displaying, on the display, an indicator of a location of the reference time point of the first found semantic data block with respect to the plurality of semantic blocks.

11. A method of providing individualized cognitive assistance, the method comprising:
receiving, by a computer, data comprising visual and audio information observed by a user, a corresponding time information, and a corresponding location information;
generating, by the computer, at least one timeline related to a time period in which the data was obtained by the user;
generating and stamping, on the at least one timeline, a plurality of consecutive episodic reference timepoints, which are spaced apart equidistant from one another;
dividing the data into a plurality of consecutive sensory data blocks, the plurality of consecutive sensory data blocks have the same predetermined size and each of the plurality of consecutive sensory data blocks comprises one reference timepoint from among the plurality of consecutive episodic reference timepoints;
generating a semantic data block for each of the plurality of consecutive sensory data blocks, wherein each of the semantic data block comprises at least one semantic cue related to a meaning of content of the respective sensory data block, and stamping the reference timepoint of the respective sensory data block onto the respective semantic data block;
displaying, in a first area of a display, the plurality of consecutive sensory data blocks and in a second area of the display, a corresponding plurality of semantic data blocks that are synchronized with the plurality of consecutive sensory data block based on the stamped reference timepoint;
displaying on a third area of the display the at least one timeline which comprises a first timeline and a second timeline, wherein the first timeline comprises the plurality of consecutive reference timepoints which are linked with the plurality of the respective sensory data blocks, and wherein the second timeline comprises a set of consecutive reference timepoints from among the plurality of consecutive reference timepoints that are linked to a set of sensory data blocks from among the plurality of the consecutive sensory data blocks, and wherein the set of sensory data blocks have been viewed by the user;

receiving an input from the user comprising a selection of a key semantic data block from among the plurality of semantic data blocks, wherein the selected key semantic data block comprises content defined by the user as useful and needed for future; and displaying a flashing dot indicating a location of the reference time point of the key semantic data block on the first timeline.

12. The method according to claim 11, further comprising:

receiving an additional input from the user comprising one of a confirmation of the flashing dot or a rejection of the flashing dot;

based on the additional input being the confirmation of the flashing dot, consecutively displaying, in the second area of the display, a set of consecutive semantic data blocks from among a plurality of consecutive semantic data blocks starting from at least one second semantic data block preceding the first reference timepoint until receiving additional input to end the displaying and consecutively displaying, in the first area of the display, a set of consecutive sensory data blocks corresponding to and in synchronization with the set of consecutive semantic data blocks; and based on the additional input being the rejection of the flashing dot, navigating to a next flashing dot from among the plurality of flashing dots, determining a next reference timepoint, and displaying a next semantic data block corresponding to the next reference timepoint in the second area of the display and the respective episodic data block in the first area of the display in synchronization with the next semantic data block.

13. A method of providing individualized cognitive assistance, the method comprising:

receiving, by a computer, data comprising visual and audio information observed by a user, a corresponding time information, and a corresponding location information;

generating, by the computer, at least one timeline related to a time period in which the data was obtained by the user;

generating and stamping, on the at least one timeline, a plurality of consecutive episodic reference timepoints, which are spaced apart equidistant from one another;

dividing the data into a plurality of consecutive sensory data blocks, the plurality of consecutive sensory data blocks have the same predetermined size and each of the plurality of consecutive sensory data blocks comprises one reference timepoint from among the plurality of consecutive episodic reference timepoints;

generating a semantic data block for each of the plurality of consecutive sensory data blocks, wherein each of the semantic data block comprises at least one semantic cue related to a meaning of content of the respective sensory data block, and stamping the reference timepoint of the respective sensory data block onto the respective semantic data block;

displaying, in a first area of a display, the plurality of consecutive sensory data blocks and in a second area of the display, a corresponding plurality of semantic data blocks that are synchronized with the plurality of consecutive sensory data block based on the stamped reference timepoint;

displaying on a third area of the display the at least one timeline which comprises a first timeline and a second timeline, wherein the first timeline comprises the plurality of consecutive reference timepoints which are linked with the plurality of the respective sensory data blocks, and wherein the second timeline comprises a set of consecutive reference timepoints from among the plurality of consecutive reference timepoints that are linked to a set of sensory data blocks from among the plurality of the consecutive sensory data blocks, and wherein the set of sensory data blocks have been viewed by the user;

receiving an input from the user comprising a first selection of a first semantic data block from among the plurality of semantic data blocks and a second selection of a second semantic data block from among the plurality of semantic data blocks, wherein the first semantic data block is a starting semantic data block and the second semantic data block is an ending semantic data block of a plurality of consecutive semantic data blocks that comprise contents defined by the user as useful and needed for future; and displaying, on the second timeline, a set of reference timepoints from a first location of the first semantic data block to a second location of the second semantic data block in a color coded highlighted portion.

14. The method according to claim 13, further comprising:

receiving an additional input from the user comprising a confirmation of the color coded highlighted portion or a rejection of the color coded highlight portion;

based on the additional input indicating the confirmation of the color coded highlighted portion, consecutively displaying a set of consecutive semantic data blocks starting from a first starting reference timepoint and ending at an ending reference timepoint of consecutive color coded highlighted data blocks in the second area of the display and consecutively displaying, in the first area of the display, a respective set of consecutive sensory data blocks corresponding to and in synchronization with the set of consecutive semantic data blocks; and based on the additional input indicating the rejection of the color coded highlighted portion, moving to a next color coded highlighted portion, determining a next starting reference timepoint of the next color coded highlighted portion, and displaying the next starting reference timepoint and next starting semantic data block corresponding to the next starting reference timepoint in the second area of the display and next starting episodic data block corresponding to and in synchronization with the next starting reference timepoint in the first area of the display.

15. An apparatus of providing individualized cognitive assistance, the apparatus comprising:

a memory configured to store computer executable instructions;

a user interface configured to receive input from a user;

a processor configured to execute the stored computer executable instructions, which when executed by the processor causes the processor to:

receive data comprising visual and audio information observed by the user, a corresponding time information, and a corresponding location information;

generate at least one timeline related to a time period in which the data was obtained by the user;

generate and stamp, on the at least one timeline, a plurality of consecutive episodic reference timepoints, which are spaced apart equidistant from one another;

divide the data into a plurality of consecutive sensory data blocks, the plurality of consecutive sensory data blocks are of the same predetermined size and each of the plurality of consecutive sensory data blocks comprises one reference timepoint from among the plurality of consecutive episodic reference timepoints;

generate a semantic data block for each of the plurality of consecutive sensory data blocks, wherein each of the semantic data block comprises at least one semantic cue related to a meaning of content of the respective sensory data block, and stamp the reference timepoint of the respective sensory data block onto the respective semantic data block; and control a display to display in a first area, the plurality of consecutive sensory data blocks and in a second area, a corresponding plurality of semantic data blocks that are synchronized with the plurality of consecutive sensory data block based on the stamped reference timepoint;

receive, via the user interface, the input from the user including at least one semantic cue;

search a plurality of consecutive semantic data blocks to find one semantic data block comprising the semantic cue that is input by the user via the user interface;

control the display to display, in the second area of the display, a first found semantic data block based on the search and control the display to display the respective sensory data block in synchronization with the first found semantic data block;

receive, via the user interface, the input from the user including one of a confirmation of the first found semantic data block or a rejection of the first found semantic data block; and based on the input comprising the rejection of the first found semantic data block, continue searching in succeeding plurality of semantic data blocks to find a next found semantic data block comprising the semantic cue that is input by the user and control the display to display the next found semantic data block in the second area of the display and the respective sensory data block in synchronization with the next found semantic data block.

16. The apparatus according to claim 15, wherein the stored computer executable instructions further cause the processor to:

generate an episodic data block for each of the plurality of consecutive sensory data blocks, the episodic data block comprises at least one episodic cue generated by simplifying a plurality of images of the visual information of the respective sensory data block from among the plurality of consecutive sensory data blocks, and to stamp the reference timepoint of the respective sensory data block onto the respective episodic data block; and control the display to display a plurality of consecutive episodic data blocks in the first area synchronized with the corresponding plurality semantic data blocks in the second area, based on the stamped reference timepoint, wherein the at least one semantic cue of the semantic data block is at least one of a blank, a text, a symbol, a flashing dot, and a color-coded highlight.

17. The apparatus of claim 15, wherein the stored computer executable instructions further cause the processor to:

based on the input comprising the confirmation of the one semantic data block, control the display to consecutively display a plurality of consecutive semantic data blocks starting from at least one first semantic data block preceding the first found semantic data block and until the input from the user comprises an instruction to end the displaying and further control the display to consecutively display, in the first area of the display, a respective plurality of consecutive sensory data blocks in synchronization with the plurality of the displayed consecutive semantic data blocks.

18. The apparatus of claim 15, wherein the visual and audio information is at least one of:

the audio information is at least one of first communication data communicated by the user during an established communication with another entity via a network or a second communication data communicated to the user by the another entity during the established communication, or the visual information is contents downloaded from the network and observed by the user.

19. The apparatus of claim 15, wherein the data observed by the user comprises at least one of:

first data including sensory data obtained from a first source and the visual and audio information comprises an environment observed by the user and the sensory data comprises cognitive state of the user with respect to the environment, or second data obtained from a second source different from the first source, the second source including multimedia data being downloaded via a network and observed by the user.

20. The apparatus of claim 15, wherein the stored computer executable instructions further cause the processor to:

to control the display to display on a third area of the display the at least one timeline which comprises a first timeline and a second timeline, wherein the first timeline comprises the plurality of consecutive reference timepoints which are linked with the plurality of the respective sensory data blocks, and wherein the second timeline comprises a set of consecutive reference timepoints from among the plurality of consecutive reference timepoints that are linked to a set of sensory data blocks from among the plurality of the consecutive sensory data blocks, wherein the set of sensory data blocks have been viewed by the user.

* * * * *